(12) United States Patent
Ferree et al.

(10) Patent No.: US 10,335,595 B2
(45) Date of Patent: *Jul. 2, 2019

(54) DYNAMIC CONTROL OF TRANSCUTANEOUS ELECTRICAL NERVE STIMULATION THERAPY USING CONTINUOUS SLEEP DETECTION

(71) Applicant: Neurometrix, Inc., Waltham, MA (US)

(72) Inventors: Thomas C. Ferree, Waltham, MA (US); Shai N. Gozani, Brookline, MA (US); Xuan Kong, Acton, MA (US)

(73) Assignee: Neurometrix, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/648,632

(22) Filed: Jul. 13, 2017

(65) Prior Publication Data

US 2017/0312515 A1    Nov. 2, 2017

Related U.S. Application Data

(63) Continuation-in-part of application No. 15/602,611, filed on May 23, 2017, which is a continuation of
(Continued)

(51) Int. Cl.
*A61B 5/00* (2006.01)
*A61N 1/36* (2006.01)
(Continued)

(52) U.S. Cl.
CPC ........ *A61N 1/36021* (2013.01); *A61B 5/1118* (2013.01); *A61B 5/1121* (2013.01);
(Continued)

(58) Field of Classification Search
CPC ............ A61N 1/36021; A61N 1/36031; A61N 1/0456; A61N 1/0476; A61N 1/37247;
(Continued)

(56) References Cited

U.S. PATENT DOCUMENTS 1,741,962 A    12/1929   Theodoropulos
D263,869 S     4/1982    Sumiyasu
(Continued)

FOREIGN PATENT DOCUMENTS

CN    1919139       2/2007
CN    101626804     1/2010
(Continued)

OTHER PUBLICATIONS

Ancoli-Israel, S. et al., The Role of Actigraphy in the Study of Sleep and Circadian Rhythms, Sleep, 2003, 26(3), p. 342-392.
(Continued)

*Primary Examiner* — Catherine M Voorhees
(74) *Attorney, Agent, or Firm* — Pandiscio & Pandiscio

(57) ABSTRACT

Apparatus for providing transcutaneous electrical nerve stimulation (TENS) therapy to a user, said apparatus comprising: a housing; an application unit for providing mechanical coupling between the housing and the user's body; a stimulation unit for electrically stimulating at least one nerve of the user; a sensing unit for (i) sensing the user's body movement and body orientation to determine whether the user is in an "out-of-bed" state or a "rest-in-bed" state, and (ii) analyzing the sleep characteristics of the user during the "rest-in-bed" state; and a feedback unit for at least one of (i) providing the user with feedback in response to the analysis of the sleep characteristics of the user, and (ii) modifying the electrical stimulation provided to the user by the stimulation unit in response to the analysis of the sleep characteristics of the user; wherein the sleep characteristics comprise a likelihood measure of the user's sleep quality.

49 Claims, 13 Drawing Sheets

Related U.S. Application Data application No. 14/610,757, filed on Jan. 30, 2015, now Pat. No. 9,656,070, which is a continuation of application No. 13/678,221, filed on Nov. 15, 2012, now Pat. No. 8,948,876, application No. 15/648,632, which is a continuation-in-part of application No. 14/980,041, filed on Dec. 28, 2015, now Pat. No. 9,731,126, which is a continuation-in-part of application No. 14/794,588, filed on Jul. 8, 2015, now Pat. No. 9,675,801, which is a continuation-in-part of application No. 14/610,757, filed on Jan. 30, 2015, now Pat. No. 9,656,070, which is a continuation of application No. 13/678,221, filed on Nov. 15, 2012, now Pat. No. 8,948,876, said application No. 14/794,588 is a continuation-in-part of application No. 14/269,887, filed on May 5, 2014, now Pat. No. 9,827,420, which is a continuation-in-part of application No. 14/230,648, filed on Mar. 31, 2014, now Pat. No. 9,474,898, and a continuation-in-part of application No. 14/253,628, filed on Apr. 15, 2014, now Pat. No. 10,279,179.

(60) Provisional application No. 61/560,029, filed on Nov. 15, 2011, provisional application No. 61/657,382, filed on Jun. 8, 2012, provisional application No. 61/806,481, filed on Mar. 29, 2013, provisional application No. 61/811,864, filed on Apr. 15, 2013, provisional application No. 61/819,159, filed on May 3, 2013, provisional application No. 61/858,150, filed on Jul. 25, 2013, provisional application No. 62/021,807, filed on Jul. 8, 2014, provisional application No. 62/213,978, filed on Sep. 3, 2015, provisional application No. 62/101,029, filed on Jan. 8, 2015, provisional application No. 62/361,693, filed on Jul. 13, 2016.

(51) Int. Cl.
*A61B 5/11* (2006.01)
*A61N 1/04* (2006.01)
*A61N 1/32* (2006.01)
*A61N 1/372* (2006.01)

(52) U.S. Cl.
CPC .......... *A61B 5/4815* (2013.01); *A61B 5/4836* (2013.01); *A61B 5/6828* (2013.01); *A61B 5/6831* (2013.01); *A61N 1/0456* (2013.01); *A61N 1/0476* (2013.01); *A61N 1/0492* (2013.01); *A61N 1/321* (2013.01); *A61N 1/36014* (2013.01); *A61N 1/36031* (2017.08); *A61N 1/37247* (2013.01); *A61B 5/0002* (2013.01); *A61B 5/1116* (2013.01); *A61N 1/36034* (2017.08)

(58) Field of Classification Search
CPC .. A61N 1/36014; A61N 1/321; A61N 1/0492; A61N 1/36034; A61B 5/6831; A61B 5/6828; A61B 5/1118; A61B 5/1121; A61B 5/4815; A61B 5/4836; A61B 5/0002; A61B 5/1116
See application file for complete search history.

(56) References Cited

U.S. PATENT DOCUMENTS

| | | |
|---|---|---|
| 4,503,863 A | 3/1985 | Katims |
| 4,605,010 A | 8/1986 | McEwen |
| 4,738,250 A | 4/1988 | Fulkerson et al. |
| 5,063,929 A | 11/1991 | Bartelt et al. |
| 5,121,747 A * | 6/1992 | Andrews ............ A61N 1/36003 602/16 |
| 5,169,384 A | 12/1992 | Bosniak et al. |
| D346,029 S | 4/1994 | Shalvi |
| 5,350,414 A | 9/1994 | Kolen |
| 5,429,589 A | 7/1995 | Cartmell et al. |
| 5,479,939 A | 1/1996 | Ogino |
| 5,487,759 A | 1/1996 | Bastyr et al. |
| 5,562,718 A | 10/1996 | Palermo |
| 5,806,522 A | 9/1998 | Katims |
| D411,887 S | 7/1999 | Agarwala |
| 5,948,000 A | 9/1999 | Larsen et al. |
| 6,099,488 A | 8/2000 | Hung |
| 6,161,044 A | 12/2000 | Silverstone |
| 6,266,558 B1 | 7/2001 | Gozani et al. |
| D450,313 S | 11/2001 | Koinuma |
| 6,430,450 B1 | 8/2002 | Bach-y-Rita et al. |
| D462,772 S | 9/2002 | Lamping et al. |
| 6,456,884 B1 | 9/2002 | Kenney |
| 6,662,051 B1 | 12/2003 | Eraker et al. |
| D541,042 S | 4/2007 | Andre et al. |
| D566,383 S | 4/2008 | Harris et al. |
| D592,200 S | 5/2009 | Liu |
| D598,556 S | 8/2009 | Chen |
| D600,352 S | 9/2009 | Cryan |
| D607,198 S | 1/2010 | Andre et al. |
| D609,353 S | 2/2010 | Cryan |
| 7,668,598 B2 | 2/2010 | Herregraven et al. |
| D611,611 S | 3/2010 | Sachi et al. |
| D615,526 S | 5/2010 | Andre et al. |
| 7,720,548 B2 | 5/2010 | King |
| 7,725,193 B1 | 5/2010 | Chu |
| 7,787,946 B2 * | 8/2010 | Stahmann ............ A61B 5/0031 607/3 |
| D625,829 S | 10/2010 | Arbesman et al. |
| D629,115 S | 12/2010 | Robertson |
| D636,881 S | 4/2011 | Clemens et al. |
| D637,988 S | 5/2011 | Jinkinson |
| 8,108,049 B2 | 1/2012 | King |
| 8,121,702 B2 | 2/2012 | King |
| 8,131,374 B2 | 3/2012 | Moore et al. |
| D658,302 S | 4/2012 | Nixon |
| D680,735 S | 4/2013 | Itabashi et al. |
| 8,421,642 B1 | 4/2013 | McIntosh et al. |
| D688,707 S | 8/2013 | Vincent et al. |
| D705,428 S | 5/2014 | Cheney et al. |
| D712,045 S | 8/2014 | Thornton |
| 8,825,175 B2 | 9/2014 | King |
| 8,862,238 B2 | 10/2014 | Rahimi et al. |
| D716,963 S | 11/2014 | Yosef et al. |
| 8,948,876 B2 | 2/2015 | Gozani et al. |
| D732,682 S | 6/2015 | Porat |
| 9,168,375 B2 | 10/2015 | Rahimi et al. |
| D744,661 S | 12/2015 | Rizzi |
| D750,263 S | 2/2016 | Shigeno et al. |
| D750,798 S | 3/2016 | Yosef et al. |
| D754,355 S | 4/2016 | Ganapathy et al. |
| D754,973 S | 5/2016 | Danze et al. |
| D757,292 S | 5/2016 | Chen |
| D758,605 S | 6/2016 | Chen |
| D758,606 S | 6/2016 | Chen |
| D759,262 S | 6/2016 | Chen |
| D759,263 S | 6/2016 | Chen |
| D759,958 S | 6/2016 | Requa |
| D762,628 S | 8/2016 | Yoon et al. |
| D762,872 S | 8/2016 | Chen |
| D767,775 S | 9/2016 | Gilmer et al. |
| 9,452,287 B2 | 9/2016 | Rosenbluth et al. |
| 9,474,898 B2 | 10/2016 | Gozani et al. |
| D774,654 S | 12/2016 | Anderson |
| D778,453 S | 2/2017 | Knaus et al. |
| D779,677 S | 2/2017 | Chen |
| 9,561,397 B2 | 2/2017 | Zaki |
| D784,544 S | 4/2017 | Dudkiewicz et al. |
| D784,546 S | 4/2017 | Gordon |
| D784,946 S | 4/2017 | Jun et al. |
| D788,056 S | 5/2017 | Choi et al. |
| 9,656,070 B2 | 5/2017 | Gozani et al. |

(56) References Cited

U.S. PATENT DOCUMENTS

| | | | |
|---|---|---|---|
| D789,546 S | 6/2017 | Matfus et al. | |
| D789,547 S | 6/2017 | Matfus et al. | |
| D791,333 S | 7/2017 | Wilson | |
| D792,363 S | 7/2017 | Kim et al. | |
| D794,331 S | 8/2017 | Grote | |
| 9,731,126 B2* | 8/2017 | Ferree | A61N 1/0476 |
| D801,542 S | 10/2017 | Anderson | |
| D802,780 S | 11/2017 | Hsu | |
| D806,669 S | 1/2018 | Kangasmaa et al. | |
| D810,843 S | 2/2018 | Karvandi | |
| D811,729 S | 3/2018 | Bysshe | |
| D813,407 S | 3/2018 | Chen | |
| D813,408 S | 3/2018 | Chen | |
| D828,569 S | 9/2018 | Mercuro | |
| D829,182 S | 9/2018 | Li | |
| D830,565 S | 10/2018 | Xu | |
| D831,017 S | 10/2018 | Choe et al. | |
| D831,221 S | 10/2018 | Smith | |
| D831,335 S | 10/2018 | Crease | |
| D832,230 S | 10/2018 | Lee et al. | |
| 2002/0010497 A1 | 1/2002 | Merfeld et al. | |
| 2003/0023192 A1 | 1/2003 | Foxlin | |
| 2003/0074037 A1 | 4/2003 | Moore et al. | |
| 2003/0114892 A1 | 6/2003 | Nathan et al. | |
| 2003/0208246 A1 | 11/2003 | Kotlik et al. | |
| 2004/0122483 A1 | 6/2004 | Nathan et al. | |
| 2005/0059903 A1 | 3/2005 | Izumi | |
| 2005/0080463 A1* | 4/2005 | Stahmann | A61B 5/0488 607/62 |
| 2006/0052788 A1 | 3/2006 | Thelen et al. | |
| 2006/0085049 A1 | 4/2006 | Cory et al. | |
| 2006/0095088 A1 | 5/2006 | De Ridder | |
| 2006/0173507 A1 | 8/2006 | Mrva et al. | |
| 2006/0190057 A1 | 8/2006 | Reese | |
| 2007/0060922 A1 | 3/2007 | Dreyfuss | |
| 2007/0276449 A1 | 11/2007 | Gunter et al. | |
| 2008/0077192 A1 | 3/2008 | Harry et al. | |
| 2008/0146980 A1 | 6/2008 | Rousso et al. | |
| 2008/0147143 A1 | 6/2008 | Popovic et al. | |
| 2008/0147146 A1 | 6/2008 | Wahlgren et al. | |
| 2008/0312709 A1 | 12/2008 | Volpe et al. | |
| 2009/0030476 A1 | 1/2009 | Hargrove | |
| 2009/0112214 A1 | 4/2009 | Philippon et al. | |
| 2009/0131993 A1 | 5/2009 | Rousso et al. | |
| 2009/0240303 A1 | 9/2009 | Wahlstrand et al. | |
| 2009/0264789 A1 | 10/2009 | Molnar et al. | |
| 2009/0270947 A1 | 10/2009 | Stone et al. | |
| 2009/0326604 A1 | 12/2009 | Tyler et al. | |
| 2010/0004715 A1 | 1/2010 | Fahey | |
| 2010/0042180 A1 | 2/2010 | Mueller et al. | |
| 2010/0057149 A1 | 3/2010 | Fahey | |
| 2010/0087903 A1 | 4/2010 | Van Herk et al. | |
| 2010/0094103 A1 | 4/2010 | Kaplan et al. | |
| 2010/0114257 A1 | 5/2010 | Torgerson | |
| 2010/0131028 A1 | 5/2010 | Hsu et al. | |
| 2010/0198124 A1 | 8/2010 | Bhugra | |
| 2010/0217349 A1 | 8/2010 | Fahey | |
| 2010/0241464 A1 | 9/2010 | Amigo et al. | |
| 2011/0066209 A1 | 3/2011 | Bodlaender et al. | |
| 2011/0224665 A1 | 9/2011 | Crosby et al. | |
| 2011/0257468 A1 | 10/2011 | Oser et al. | |
| 2011/0264171 A1 | 10/2011 | Torgerson | |
| 2011/0276107 A1 | 11/2011 | Simon et al. | |
| 2011/0282164 A1 | 11/2011 | Yang et al. | |
| 2012/0010680 A1 | 1/2012 | Wei et al. | |
| 2012/0108998 A1 | 5/2012 | Molnar et al. | |
| 2013/0096641 A1 | 4/2013 | Strother et al. | |
| 2013/0158627 A1 | 6/2013 | Gozani et al. | |
| 2013/0217998 A1* | 8/2013 | Mahfouz | G16H 50/50 600/409 |
| 2014/0039450 A1 | 2/2014 | Green et al. | |
| 2014/0057232 A1* | 2/2014 | Wetmore | G09B 19/00 434/236 |
| 2014/0081353 A1 | 3/2014 | Cook et al. | |
| 2014/0107729 A1 | 4/2014 | Sumners et al. | |
| 2014/0163444 A1 | 6/2014 | Ingvarsson et al. | |
| 2014/0245791 A1 | 9/2014 | Proud et al. | |
| 2014/0276549 A1 | 9/2014 | Osorio | |
| 2014/0296934 A1 | 10/2014 | Gozani et al. | |
| 2014/0296935 A1 | 10/2014 | Ferree et al. | |
| 2014/0309709 A1* | 10/2014 | Gozani | A61N 1/36021 607/46 |
| 2014/0336730 A1 | 11/2014 | Simon et al. | |
| 2014/0379045 A1 | 12/2014 | Rahimi et al. | |
| 2015/0045853 A1 | 2/2015 | Alataris et al. | |
| 2015/0174402 A1 | 6/2015 | Thomas et al. | |
| 2015/0321000 A1 | 11/2015 | Rosenbluth et al. | |
| 2015/0328467 A1 | 11/2015 | Demers et al. | |
| 2015/0335288 A1 | 11/2015 | Toth et al. | |
| 2016/0367823 A1 | 12/2016 | Cowan et al. | |
| 2018/0177996 A1 | 6/2018 | Gozani et al. | |

FOREIGN PATENT DOCUMENTS

| | | | |
|---|---|---|---|
| CN | 102355847 | 2/2012 | |
| CN | 102740919 | 10/2012 | |
| DE | 102010052710 | 5/2012 | |
| JP | 61-171943 | 10/1986 | |
| JP | 4-347140 | 12/1992 | |
| JP | 9-117453 | 5/1997 | |
| JP | 2000-167067 | 6/2000 | |
| JP | 2005-34402 | 2/2005 | |
| JP | 2005-81068 | 3/2005 | |
| JP | 2006-68300 | 3/2006 | |
| JP | 418546 | 9/2008 | |
| WO | WO 97/42999 | 11/1997 | |
| WO | WO 99/64105 | 12/1999 | |
| WO | WO 03051453 A2* | 6/2003 | A61N 1/0452 |
| WO | WO 2004/078132 | 9/2004 | |
| WO | WO 2007/061746 | 5/2007 | |
| WO | WO 2008/079757 | 7/2008 | |
| WO | WO 2008/088985 | 7/2008 | |
| WO | WO 2011/075179 | 6/2011 | |
| WO | WO 2011/137193 | 11/2011 | |
| WO | WO 2012/116407 | 9/2012 | |

OTHER PUBLICATIONS

Barbarisi, Manlio et al., Pregabalin and Transcutaneous Electrical Nerve Stimulation for Postherpetic Neuralgia Treatment, The Clinical Journal of Pain, Sep. 2010;26(7):567-572.

Bjordal JM et al., Transcutaneous electrical nerve stimulation (TENS) can reduce postoperative analgesic consumption. A meta-analysis with assessment of optimal treatment parameters for postoperative pain, European Journal of Pain, 2003, vol. 7(2): 181-188.

Bloodworth DM et al., Comparison of stochastic vs. conventional transcutaneous electrical stimulation for pain modulation in patients with electromyographically documented radiculopathy. American Journal of Physical Medicine & Rehabilitation, 2004, vol. 83(8): 584-591.

Chandran P et al., Development of opioid tolerance with repeated transcutaneous electrical nerve stimulation administration, Pain, 2003, vol. 102: 195-201.

Chen CC et al., A comparison of transcutaneous electrical nerve stimulation (TENS) at 3 and 80 pulses per second on cold-pressor pain in healthy human participants, Clinical Physiology and Functioning Imaging, 2010, vol. 30(4): 260-268.

Chen CC et al., An investigation into the effects of frequency-modulated transcutaneous electrical nerve stimulation (TENS) on experimentally-induced pressure pain in healthy human participants, The Journal of Pain, 2009, vol. 10(10): 1029-1037.

Chen CC et al., Differential frequency effects of strong nonpainful transcutaneous electrical nerve stimulation on experimentally induced ischemic pain in healthy human participants, The Clinical Journal of Pain, 2011, vol. 27(5): 434-441.

Chen CC et al., Does the pulse frequency of transcutaneous electrical nerve stimulation (TENS) influence hypoalgesia? A systematic review of studies using experirnantal pain and healthy human participants, Physiotherapy, 2008, vol. 94: 11-20.

(56) References Cited

OTHER PUBLICATIONS

Claydon LS et al., Dose-specific effects of transcutaneous electrical nerve stimulation on experimental pain, Clinical Journal of Pain, 2011, vol. 27(7): 635-647.

Cole, R.J. et al., Automatic Sleep/Wake Identification From Wrist Activity, Sleep, 1992, 15(5), p. 461-469.

Cruccu G. et al., EFNS guidelines on neurostimulation therapy for neuropathic pain, European Journal of Neurology, 2007, vol. 14: 952-970.

Davies Hto et al., Diminishing returns or appropriate treatment strategy?—an analysis of short-term outcomes after pain clinic treatment, Pain, 1997, vol. 70: 203-208.

DeSantana JM et al., Effectiveness of transcutaneous electrical nerve stimulation for treatment of hyperalgesia and pain, Curr Rheumatol Rep. 2008, vol. 10(6): 492-499.

Dubinsky RM et al., Assessment: Efficacy of transcutaneous electric nerve stimulation in the treatment of pain in neurologic disorders (an evidence-based review): Report of the therapeutics and technology assessment subcommittee of the american academy of neurology, Neurology, 2010, vol. 74: 173-176.

Fary RE et al., Monophasic electrical stimulation produces high rates of adverse skin reactions in healthy subjects, Physiotherapy Theory and Practice, 2011, vol. 27(3): 246-251.

Fishbain, David A. et al. Does Fain Mediate the Pain Interference with Sleep Problem in Chronic Pain? Findings from Studies for Management of Diabetic Peripheral Neuropathic Pain with Duloxetine, Journal of Pain Symptom Management, Dec. 2008;36(6):639-647.

Fishbain, David A. et al., Transcutaneous Electrical Nerve Stimulation (TENS) Treatment Outcome in Long-Term Users, The Clinical Journal of Pain, Sep. 1996;12(3):201-214.

Food and Drug Administration, Draft Guidance for Industry and Staff: Class II Special Controls Guidance Document: Transcutaneous Electrical Nerve Stimulator for Pain Relief, Apr. 5, 2010.

Garrison DW et al., Decreased activity of spontaneous and noxiously evoked dorsal horn cells during transcutaneous electrical nerve stimulation (TENS), Pain, 1994, vol. 58: 309-315.

Gilron, I. et al., Chronobiological Characteristics of Neuropathic Pain: Clinical Predictors of Diurnal Pain Rhythmicity, The Clinical Journal of Pain, 2013.

Hori, T. et al., Skin Potential Activities and Their Regional Differences During Normal Sleep in Humans, The Japanese Journal of Physiology, 1970, vol. 20, p. 657-671.

Jelinek HF et al., Electric pulse frequency and magnitude of perceived sensation during electrocutaneous forearm stimulation, Arch Phys Med Rehabil, 2010, vol. 91: 1372-1382.

Jin DM et al., Effect of transcutaneous electrical nerve stimulation on symptomatic diabetic peripheral neuropathy: a meta-analysis of randomized controlled trials, Diabetes Research and Clinical Practice, 2010, vol. 89: 10-15.

Johnson MI et al., Analgesic effects of different frequencies of transcutaneous electrical nerve stimulation on cold-induced pain in normal subjects, Pain, 1989, vol. 39: 231-236.

Johnson MI et al., Transcutaneous Electrical Nerve Stimulation (TENS) and TENS-like devices: do they provide pain relief?, Pain Reviews, 2001, vol. 8: 7-44.

Johnson MI et al., Transcutaneous electrical nerve stimulation for the management of painful conditions: focus on neuropathic pain, Expert Review of Neurotherapeutics, 2011, vol. 11(5): 735-753.

Johnson, M.I. et al., An in-depth study of long-term users of transcutaneous electrical nerve stimulation (TENS). Implications for clinical use of TENS. Pain. Mar. 1991;44(3):221-229.

Kaczmarek, Kurt A. et al.. Electrotactile and Vibrotactile Displays for Sensory Substitution Systems. IEEE Trans. Biomed, Eng. Jan. 1991;38 (1):1-16.

Kantor G et al., The effects of selected stimulus waveforms on pulse and phase characteristics at sensory and motor thresholds, Physical Therapy, 1994, vol. 74(10): 951-962.

Keller, Thierry et al., Electrodes for transcutaneous (surface) electrical stimulation, J. Automatic Control, University of Belgrade. 2008;18(2):35-45.

Koumans, A. J. R. et al., Electrodermal Levels and Fluctuations During Normal Sleep, Psychophysiology, 1968, 5(3), p. 300-306.

Kripke, D.F. et al., Wrist Actigraphic Scoring for Sleep Laboratory Patients: Algorithm Development, Journal of Sleep Research, 2010, 19(4), p. 612-619.

Law PPW et al., Optimal stimulation frequency of transcutaneous electrical nerve stimulation on people with knee osteoarthritis, J Rehabil Med, 2004, vol. 36: 220-225.

Leonard G et al., Deciphering the role of endogenous opioids in high-frequency TENS using low and high doses of naloxone, Pain, 2010, vol. 151: 215-219.

Levy et al., A comparison of two methods for measuring thermal thresholds in diabetic neuropathy, Journal of Neurology, Neurosurgery, and Psychiatry, 1989, vol. 52: 1072-1077.

Lykken, D.T., Properties of Electrodes Used in Electrodermal Measurement, J. Comp. Physiol. Psychol. Oct. 1959;52:629-634.

Lykken, D.T., Square-Wave Analysis of Skin Impedance. Psychophysiology. Sep. 1970;7(2):262-275.

Melzack R et al., Pain mechanisms: A New Theory, Science, 1965, vol. 150(3699): 971-979.

Moran F et al., Hypoalgesia in response to transcutaneous electrical nerve stimulation (TENS) depends on stimulation intensity, The Journal of Pain, 2011, vol. 12(8): 929-935.

Oosterhof, Jan et al., Outcome of transcutaneous electrical nerve stimulation in chronic pain: short-term results of a double-blind, randomised, placebo-controlled trial. J. Headache Pain. Sep. 2006;7(4):196-205.

Oosterhof, Jan et al., The long-term outcome of transcutaneous electrical nerve stimulation in the treatment for patients with chronic pain: a randomized, placebo-controlled trial. Pain Pract. Sep. 2012;12(7):513-522.

Pantaleao MA et al., Adjusting pulse amplitude during transcutaneous electrical nerve stimulation (TENS) application produces greater hypoalgesia, The Journal of Pain, 2011, vol. 12(5): 581-590.

Paquet, J. et al., Wake Detection Capacity of Actigraphy During Sleep, Sleep, 2007, 30(10), p. 1362-1369.

Pieber K et al., Electrotherapy for the treatment of painful diabetic peripheral neuropathy: a review, Journal of Rehabilitation Medicine, 2010, vol. 42: 289-295.

Raskin, J. et al., A Double-Blind, Randomized Multicenter Trial Comparing Duloxetine with Placebo in the Management of Diabetic Peripheral Neuropathic Pain, Pain Medicine, 2005, 6(5), p. 346-356.

Sadeh, A., The Role and Validity of Actigraphy in Sleep Medicine: An Update, Sleep Medicine Reviews, 2011, vol. 15, p. 259-267.

Sadosky, A. et al., Burden of Illness Associated with Painful Diabetic Peripheral Neuropathy Among Adults Seeking Treatment in the US: Results from a Retrospective Chart Review and Cross-Sectional Survey, Diabetes, Metabolic Syndrome and Obesity: Targets and Therapy, 2013, vol. 6, p. 79-92.

Scherder, E. J. A. et al., Transcutaneous Electrical Nerve Stimulation (TENS) Improves the Rest-Activity Rhythm in Midstage Alzheimer's Disease, Behavioral Brain Research, 1999, vol. 101, p. 105-107.

Tryon, W. W., Issues of Validity in Actigraphic Sleep Assessment, Sleep, 2004, 27(1), p. 158-165.

Tsai, Y. et al., Impact of Subjective Sleep Quality on Glycemic Control in Type 2 Diabetes Mellitus, Family Practice, 2012, vol. 29, p. 30-35.

Van Boxtel, A., Skin resistance during square-wave electrical pulses of 1 to 10 mA. Med. Biol. Eng. Comput. Nov. 1977;15(6):679-687.

Van Someren, E. J. W. et al., Gravitational Artefact in Frequency Spectra of Movement Acceleration: Implications for Actigraphy in Young and Elderly Subjects, Journal of Neuroscience Methods, 1996, vol. 65, p. 55-62.

Webster, J. B. et al., An Activity-Based Sleep Monitor System for Ambulatory Use, Sleep, 1982, 5(4), p. 389-399.

Zelman, D. C. et al., Sleep Impairment in Patients With Painful Diabetic Peripheral Neuropathy, The Clinical Journal of Pain, 2006, 22(8), p. 681-685.

Aurora, R. et al., The Treatment of Restless Legs Syndrome and Periodic Limb Movement Disorder in Adults—An Update for 2012: Practice Parameters with an Evidence-Based Systematic Review and Meta-Analyses, Sleep, 2012, vol. 35, No. 8, p. 1039-1062.

(56) References Cited

OTHER PUBLICATIONS

Bonnet, M. et al., Recording and Scoring Leg Movements, Sleep, 1993, vol. 16, No. 8, p. 748-759.

Boyle, J. et al., Randomized, Placebo-Controlled Comparison of Amitriptyline, Duloxetine, and Pregabalin in Patients With Chronic Diabetic Peripheral Neuropathic Pain, Diabetes Care, 2012, vol. 35, p. 2451-2458.

Kovacevic-Ristanovic, R. et al., Nonpharmacologic Treatment of Periodic Leg Movements in Sleep, Arch. Phys. Med. Rehabil., 1991, vol. 72, p. 385-389.

Lopes, L. et al., Restless Legs Syndrome and Quality of Sleep in Type 2 Diabetes, Diabetes Care, 2005, vol. 28, No. 11, p. 2633-2636.

Nightingale, S., The neuropathic pain market, Nature Reviews, 2012, vol. 11, p. 101-102.

Zucconi, M. et al., The official World Association of Sleep Medicine (WASM) standards for recording and scoring periodic leg movements in sleep (PLMS) and wakefulness (PLMW) developed in collaboration with a task force from the International Restless Legs Syndrome Study Group (IRLSSG), Sleep Medicine, 2006, vol. 7, p. 175-183.

Sheridan et al., Some Factors Influencing the Threshold of the Electrocutaneous Stimulus, Perceptual and Motor Skills, 1966, vol. 22, pp. 647-654.

Susi et al., Motion Mode Recognition and Step Detection Algorithms for Mobile Phone Users, Sensors, Jan. 24, 2013, vol. 13, pp. 1539-1562.

Amazon, "Quell 2.0 Wearable Pain Relief Technology", Sep. 15, 2018. http://www.amazon/com/Quell-Wearable-Pain-Relief-Technology/dp/B07DHW2MJJ/ref=cm_cr_arp_d_product_top?le.UTF8. Shown on p. 1. (Year: 2018).

Amazon, "Quell Wearable Pain Relief Technology Starter Kit", Oct. 18, 2017. http://www.amazon.com/Quell-Wearable-ReliefTechnology-Starter/dp/B075YVCLZT/ref=cm_cr_arp_d_product_top?ie=UTF8. Shown on p. 1. (Year: 2017).

\* cited by examiner

DYNAMIC CONTROL OF TRANSCUTANEOUS ELECTRICAL NERVE STIMULATION THERAPY USING CONTINUOUS SLEEP DETECTION

REFERENCE TO PENDING PRIOR PATENT APPLICATIONS

This patent application:
(1) is a continuation-in-part of pending prior U.S. patent application Ser. No. 15/602,611, filed May 23, 2017 by NeuroMetrix, Inc. and Shai N. Gozani et al. for APPARATUS AND METHOD FOR RELIEVING PAIN USING TRANSCUTANEOUS ELECTRICAL NERVE STIMULATION, which patent application:
  (A) is a continuation of prior U.S. patent application Ser. No. 14/610,757, filed Jan. 30, 2015 by NeuroMetrix, Inc. and Shai N. Gozani et al. for APPARATUS AND METHOD FOR RELIEVING PAIN USING TRANSCUTANEOUS ELECTRICAL NERVE STIMULATION, which patent application in turn:
    (i) is a continuation of prior U.S. patent application Ser. No. 13/678,221, filed Nov. 15, 2012 by NeuroMetrix, Inc. and Shai N. Gozani et al. for APPARATUS AND METHOD FOR RELIEVING PAIN USING TRANSCUTANEOUS ELECTRICAL NERVE STIMULATION, which in turn claims benefit of:
      (a) prior U.S. Provisional Patent Application Ser. No. 61/560,029, filed Nov. 15, 2011 by Shai N. Gozani for SENSUS OPERATING MODEL; and
      (b) prior U.S. Provisional Patent Application Ser. No. 61/657,382, filed Jun. 8, 2012 by Shai N. Gozani et al. for APPARATUS AND METHOD FOR RELIEVING PAIN USING TRANSCUTANEOUS ELECTRICAL NERVE STIMULATION;
(2) is a continuation-in-part of pending prior U.S. patent application Ser. No. 14/980,041, filed Dec. 28, 2015 by NeuroMetrix, Inc. and Thomas Ferree et al. for TRANSCUTANEOUS ELECTRICAL NERVE STIMULATOR WITH AUTOMATIC DETECTION OF LEG ORIENTATION AND LEG MOTION FOR ENHANCED SLEEP ANALYSIS, INCLUDING ENHANCED TRANSCUTANEOUS ELECTRICAL NERVE STIMULATION (TENS) USING THE SAME, which patent application:
  (A) is a continuation-in-part of prior U.S. patent application Ser. No. 14/794,588, filed Jul. 8, 2015 by NeuroMetrix, Inc. and Xuan Kong et al. for MEASURING THE "ON-SKIN" TIME OF A TRANSCUTANEOUS ELECTRICAL NERVE STIMULATOR (TENS) DEVICE IN ORDER TO MINIMIZE SKIN IRRITATION DUE TO EXCESSIVE UNINTERRUPTED WEARING OF THE SAME, which patent application:
    (i) is a continuation-in-part of prior U.S. patent application Ser. No. 14/610,757, filed Jan. 30, 2015 by NeuroMetrix, Inc. and Shai N. Gozani et al. for APPARATUS AND METHOD FOR RELIEVING PAIN USING TRANSCUTANEOUS ELECTRICAL NERVE STIMULATION, which patent application:
      (a) is a continuation of prior U.S. patent application Ser. No. 13/678,221, filed Nov. 15, 2012 by NeuroMetrix, Inc. and Shai N. Gozani et al. for APPARATUS AND METHOD FOR RELIEVING PAIN USING TRANSCUTANEOUS ELECTRICAL NERVE STIMULATION, which patent application claims benefit of:
        (1) prior U.S. Provisional Patent Application Ser. No. 61/560,029, filed Nov. 15, 2011 by Shai N. Gozani for SENSUS OPERATING MODEL; and
        (2) prior U.S. Provisional Patent Application Ser. No. 61/657,382, filed Jun. 8, 2012 by Shai N. Gozani et al. for APPARATUS AND METHOD FOR RELIEVING PAIN USING TRANSCUTANEOUS ELECTRICAL NERVE STIMULATION;
    (ii) is a continuation-in-part of pending prior U.S. patent application Ser. No. 14/269,887, filed May 5, 2014 by NeuroMetrix, Inc. and Thomas Ferree et al. for TRANSCUTANEOUS ELECTRICAL NERVE STIMULATOR WITH USER GESTURE DETECTOR AND ELECTRODE-SKIN CONTACT DETECTOR, WITH TRANSIENT MOTION DETECTOR FOR INCREASING THE ACCURACY OF THE SAME, which patent application:
      (a) is a continuation-in-part of prior U.S. patent application Ser. No. 14/230,648, filed Mar. 31, 2014 by Neurometrix, Inc. and Shai Gozani et al. for DETECTING CUTANEOUS ELECTRODE PEELING USING ELECTRODE-SKIN IMPEDANCE, which claims benefit of:
        (1) prior U.S. Provisional Patent Application Ser. No. 61/806,481, filed Mar. 29, 2013 by NeuroMetrix, Inc. and Shai Gozani for DETECTING ELECTRODE PEELING BY RELATIVE CHANGES IN SKIN-ELECTRODE IMPEDANCE;
      (b) is a continuation-in-part of pending prior U.S. patent application Ser. No. 14/253,628, filed Apr. 15, 2014 by Neurometrix, Inc. and Shai Gozani et al. for TRANSCUTANEOUS ELECTRICAL NERVE STIMULATOR WITH AUTOMATIC DETECTION OF USER SLEEP-WAKE STATE, which claims benefit of:
        (1) prior U.S. Provisional Patent Application Ser. No. 61/811,864, filed Apr. 15, 2013 by Neurometrix, Inc. and Shai Gozani for TRANSCUTANEOUS ELECTRICAL NERVE STIMULATOR WITH AUTOMATIC DETECTION OF PATIENT SLEEP-WAKE STATE;
      (c) claims benefit of prior U.S. Provisional Patent Application Ser. No. 61/819,159, filed May 3, 2013 by Neurometrix, Inc. and Thomas Ferree et al. for TAP DETECTOR WITH HIGH SENSITIVITY AND SPECIFICITY FOR A WEARABLE TRANSCUTANEOUS ELECTRICAL NERVE STIMULATOR; and
      (d) claims benefit of prior U.S. Provisional Patent Application Ser. No. 61/858,150, filed Jul. 25, 2013 by Neurometrix, Inc. and Andres Aguirre et al. for MOVEMENT REGULATED TRIP CONDITIONS IN A WEARABLE TRANSCUTANEOUS ELECTRICAL NERVE STIMULATOR;
    (iii) claims benefit of prior U.S. Provisional Patent Application Ser. No. 62/021,807, filed Jul. 8, 2014 by Neurometrix, Inc. and Xuan Kong et al. for MEASURING TENS DEVICE ON-SKIN TIME TO PREVENT AND MINIMIZE SKIN IRRITATION;
  (B) claims benefit of prior U.S. Provisional Patent Application Ser. No. 62/213,978, filed Sep. 3, 2015 by Neurometrix, Inc. and Thomas Ferree et al. for TRANSCUTANEOUS ELECTRICAL NERVE STIMULATOR WITH AUTOMATIC DETECTION OF LEG ORIENTATION AND ROTATION FOR ENHANCED SLEEP ANALYSIS; and (C) claims benefit of prior U.S. Provisional Patent Application Ser. No. 62/101,029, filed Jan. 8, 2015 by Neurometrix, Inc. and Shai Gozani et al. for METHOD AND APPARATUS FOR USING TRANSCUTANEOUS ELECTRICAL NERVE STIMULATION TO AID SLEEP;

(3) claims benefit of pending prior U.S. Provisional Patent Application Ser. No. 62/361,693, filed Jul. 13, 2016 by Neurometrix, Inc. and Thomas C. Ferree et al. for DYNAMIC CONTROL OF TENS THERAPY USING CONTINUOUS SLEEP DETECTION.

The eighteen (18) above-identified patent applications are hereby incorporated herein by reference.

FIELD OF THE INVENTION

This invention relates generally to Transcutaneous Electrical Nerve Stimulation (TENS) devices that deliver electrical currents across the intact skin of a user via electrodes so as to provide symptomatic relief of pain. More specifically, this invention relates to a TENS device worn during sleep, and a method for controlling the timing and the intensity of TENS therapeutic stimulation based on continuous real-time sleep analysis.

BACKGROUND OF THE INVENTION

Chronic pain due to diabetic neuropathy and other causes can interfere with sleep, which carries a host of secondary complications. Transcutaneous electrical nerve stimulation (TENS) devices provide pain relief by stimulating sensory nerves, which leads to an increase in endogenous opioids and down-regulation of pain signal transmission to the brain.

The most common form of TENS is commonly referred to as "conventional TENS". With a conventional TENS device, an electrical circuit generates stimulation current pulses with specified characteristics. The pulse waveform characteristics include intensity (mA), duration (μsec) and shape (typically monophasic or biphasic). The pulse pattern characteristics include the frequency (Hz) of the stimulation pulses and the length of each continuous stimulation session (minutes). These parameters are correlated to the therapeutic dose. For example, higher amplitude and longer pulses (i.e., larger pulse charge) increase the dose, whereas shorter stimulation sessions decrease the dose. Clinical studies suggest that pulse charge and stimulation session duration have the greatest impact on therapeutic dose.

Electrical stimulation is typically delivered to the user through electrodes, with the electrical stimulation being in the form of low intensity (typically less than 100 mA), short duration (typically 50-400 μsec) pulses at frequencies typically between about 10 and 200 Hz. The electrodes are placed on the skin of the user. The electrodes typically utilize hydrogels to create a stable low-impedance electrode-skin interface to facilitate the delivery of electrical current to the user so as to stimulate peripheral sensory nerves, whereby to suppress pain.

Poor sleep quality is one of the major causes of morbidity in patients suffering from chronic pain [Fishbain D A, Hall J, Meyers A L, Gonzales J, Mallinckrodt C. Does pain mediate the pain interference with sleep problem in chronic pain? Findings from studies for management of diabetic peripheral neuropathic pain with duloxetine. *J Pain Symptom Manage*. December 2008; 36(6):639-647]. It is, therefore, desirable for chronic pain sufferers to have the option of receiving TENS therapy during sleep. In fact, several studies have shown that TENS therapy can improve sleep quality (see, for example, Barbarisi M, Pace M C, Passavanti M B, et al. Pregabalin and transcutaneous electrical nerve stimulation for postherpetic neuralgia treatment. *Clin J Pain*. September 2010; 26(7):567-572).

A TENS device which could be used during sleep would offer unique opportunities to provide pain relief during bedtime with the goal of improving sleep. However, most TENS devices are designed to operate exclusively during the day (i.e., wake state) without any nighttime (i.e., sleep state) operation. This limitation is evident in the design of conventional TENS devices, in which the electric current is delivered by a stimulator through wires (called leads) that are connected to electrode pads on the skin. Such a design is not practical or safe for use during sleep because the leads are cumbersome and may get tangled or pulled, and because the electrode pads can potentially peel off the skin (which will terminate TENS therapy) or, perhaps worse, can potentially partially peel off the skin, leading to increased current density and negative consequences for the user (e.g., discomfort or, in extreme cases, burns).

In prior U.S. patent application Ser. No. 14/230,648, filed Mar. 31, 2014 by NeuroMetrix, Inc. and Shai Gozani et al. for DETECTING CUTANEOUS ELECTRODE PEELING USING ELECTRODE-SKIN IMPEDANCE, issued as U.S. Pat. No. 9,474,898 on Oct. 25, 2016, which patent is hereby incorporated herein by reference, there is disclosed a novel TENS device which allows TENS therapy to be applied during nighttime (i.e., during sleep state) as well as during the day (i.e., wake state). The key design elements that make this novel TENS device suitable for use during sleep are (1) the leads are eliminated because the electrode pads are attached directly to the housing containing the TENS stimulation circuitry, (2) the TENS housing and electrode pads are held reliably and comfortably against the skin by an adjustable strap or band, (3) the TENS device continuously measures skin-electrode contact impedance (and related electrical parameters) so as to detect if the electrode pads peel (completely or partially) off the skin and the TENS device stops delivering current if peeling is detected, (4) therapeutic stimulation may be scheduled in one-hour on-off blocks so as to provide pain relief throughout the night, and (5) the TENS device detects when the user is asleep and reduces the therapeutic stimulation level automatically so as not to disturb sleep.

The novel TENS device disclosed in prior U.S. patent application Ser. No. 14/230,648, filed Mar. 31, 2014 by NeuroMetrix, Inc. and Shai Gozani et al. for DETECTING CUTANEOUS ELECTRODE PEELING USING ELECTRODE-SKIN IMPEDANCE, issued as U.S. Pat. No. 9,474,898 on Oct. 25, 2016, which patent is hereby incorporated herein by reference, is designed to be located on the upper calf of the user. This is for three reasons. First, the TENS device needs to stimulate sensory nerve fibers in order to provide widespread pain relief through the systemic effect of an increase in endogenous opioids and down-regulation of pain signal transmission. The upper calf area has a cluster of sensory nerve fibers that can be activated easily with a transcutaneous electrical nerve stimulator because of their proximity to the surface of the skin. Second, some forms of chronic pain (such as that due to diabetic neuropathy) are experienced most acutely in the feet, and in addition to the mechanism of pain suppression through endogenous opioids described above (which is systemic), there is also evidence for additional mechanisms of pain suppression that are more local, thus making it advantageous to place the TENS device on the upper calf of the user. Third, chronic pain can be persistent throughout the day, often worsening at night, and wearing the TENS device on the upper calf makes it discreet and unobtrusive, which encourages more regular use.

In pending prior U.S. patent application Ser. No. 14/253,628, filed Apr. 15, 2014 by NeuroMetrix, Inc. and Shai Gozani et al. for TRANSCUTANEOUS ELECTRICAL NERVE STIMULATOR WITH AUTOMATIC DETECTION OF USER SLEEP-WAKE STATE, published as U.S. Patent Application Publication No. US 2014/0309709 on Oct. 16, 2014, which patent application is hereby incorporated herein by reference, there is disclosed a TENS device which is designed for use during sleep. This TENS device detects when the user is asleep and adjusts the therapeutic stimulation level to optimize therapy according to user preferences and simultaneously to avoid disturbing sleep.

In pending prior U.S. patent application Ser. No. 14/980,041, filed Dec. 28, 2015 by NeuroMetrix, Inc. and Thomas Ferree et al. for TRANSCUTANEOUS ELECTRICAL NERVE STIMULATOR WITH AUTOMATIC DETECTION OF LEG ORIENTATION AND LEG MOTION FOR ENHANCED SLEEP ANALYSIS, INCLUDING ENHANCED TRANSCUTANEOUS ELECTRICAL NERVE STIMULATION (TENS) USING THE SAME, published as U.S. Patent Application Publication No. US 2016/0144174 on May 26, 2016, which patent application is hereby incorporated herein by reference, a novel TENS device is disclosed which may be used to improve sleep quality and to also quantify sleep quality and sleep disorders, since users will be more likely to use the TENS device if they are aware of, and convinced of, its benefit to their sleep.

The gold standard in determining the sleep-wake state of a subject is polysomnography which comprises at least three distinct types of data, i.e., electroencephalogram (EEG), electrooculography (EOG) and electromyography (EMG). Because of the difficulty in recording and analyzing these types of data, actigraphy has been developed and refined over the last 30 years as a practical alternative to study sleep/awake patterns. Actigraphy is a continuous recording of body movement by means of a body-worn device, typically equipped with accelerometers [Ancoli-Israel S, Cole R, Alessi C, Chambers M, Moorcroft W, Pollak C P. The role of actigraphy in the study of sleep and circadian rhythms. *Sleep*. May 1, 2003; 26(3):342-392].

Wearable electronic devices for health and fitness have become widespread, and most have accelerometers and, from acceleration data, compute various metrics of activity to track daytime activities and/or to quantify sleep patterns. Most of these actigraphy-based devices are worn on the wrist however, and in certain ways that limits their ability to detect and quantify sleep.

Significantly, it has now been recognized that the placement of a novel, accelerometer-equipped TENS device on the upper calf of a user, with tight mechanical coupling to the upper calf of the user, may be used to support novel approaches for detecting when the user is asleep, and novel metrics for analyzing the sleep of the user, and novel means to quantify body and leg motions associated with poor sleep quality and/or disorders such as restless leg syndrome, and novel methods for providing enhanced TENS therapy using the same. Among these novel metrics are "leg movements", "body roll events" associated with rolling over in bed, and "time-on-back" data which is relevant to users suffering not only from chronic pain, but also from problematic sleep positions which can cause snoring or sleep apnea. In addition to tracking and reporting such sleep indicators, real-time feedback to the user, based on indicator trends, can also help the user to improve sleep quality. By way of example but not limitation, the novel device may be configured to provide an alert (e.g., via mechanical or electrical means on TENS device 100 or via a smartphone or another connected device) to the user when the time-on-back duration exceeds a threshold. By way of further example but not limitation, the novel device may be configured to modify TENS stimulation parameters when leg movement patterns associated with discomfort caused by nighttime pain are detected in order to enhance the analgesic effect of TENS therapy.

SUMMARY OF THE INVENTION

The preferred stimulation parameters for TENS therapy may be different during the day than the preferred stimulation parameters at night. For example, a lower stimulation intensity is generally preferred at night (i.e., during sleep) so as to decrease the likelihood that TENS stimulation interferes with sleep. Users may also achieve adequate analgesia with shorter stimulation sessions and/or longer inter-sessions intervals.

It may also be desirable for TENS parameters to be adaptively adjusted in real-time based on a user's sleep characteristics. The present invention discloses a method for adjusting TENS parameters adaptively based on the user's sleep patterns. Other measurements that may be used to modify overnight TENS parameters include, but are not limited to, user skin temperature and temperature changes, skin impedance and impedance changes, heart rate and heart rate variability, electroencephalograph (EEG) patterns and pattern changes, breathing patterns and pattern changes, and/or electrooculography (EOG) characteristics and patterns.

Thus, the present invention comprises the provision and use of a novel TENS device which comprises a TENS stimulator designed to be placed on the user's upper calf (or other anatomical location) and a pre-configured electrode array designed to provide circumferential stimulation to at least one nerve within the upper calf of the user (or other anatomical location). A three-axis accelerometer incorporated into the TENS device measures the projection of static gravity onto each axis, which depends on body orientation, and the time-varying acceleration on each axis, due to linear or rotational motion of the body. Acceleration is measured in units of g (standard earth gravity). Alternatively and/or additionally, a three-axis gyroscope can be incorporated into the TENS device and can provide information about orientation and rotational motion of the body.

The placement of the novel TENS device on the upper calf of the user supports novel approaches for detecting when the user is asleep, and for quantifying sleep and assessing abnormal body and leg motions, and for providing enhanced TENS therapy using such sleep analysis.

First, the novel TENS device measures leg orientation, which is highly correlated with body orientation and therefore indicative of the user's recumbent state (and thereby the user's sleep-wake state). Specifically, the novel TENS device measures two distinct aspects of leg orientation: leg "elevation" (or the angle of the lower leg relative to the horizontal), and leg "rotation" (or the angle of rotation of the lower leg about its own axis).

Second, the novel TENS device measures leg motion, which is also indicative of the user's sleep-wake state. Specifically, the novel TENS device measures two distinct aspects of leg motion: "net activity" (which is the magnitude of movement-related acceleration averaged within one-minute windows), and "leg movements" (or brief events that are known to occur in sleep but are not evident in net activity). Some leg movements accompanied by a large leg rotation may be further classified as "body roll events" (such as occur when rolling over in bed). Repetitive leg movements may occur in people with chronic pain and other medical conditions, and may degrade the quality of sleep experienced by the person (and his/her sleep partner). Quantification and monitoring of the repetitive leg movements may provide insights to these conditions and trends of these conditions.

Third, the novel TENS device combines these two measures of leg orientation (i.e., leg elevation and leg rotation) and two measures of leg motion (i.e., net activity and leg movements) to improve sleep quantification and to utilize more precise quantification metrics to enhance therapeutic benefits.

Based on body activity, elevation, and/or position measurements, TENS stimulation parameters are adaptively adjusted to the user's sleep characteristics and the user's potential needs for TENS stimulation therapy to control pain. To minimize nerve habituation, TENS is most effective if it is used according to a schedule which includes stimulation sessions and breaks between those stimulation sessions. In normal daytime use, one-hour stimulation sessions are separated by one-hour breaks. In one embodiment of the present invention, the stimulation session duration is reduced from 60 minutes to 30 minutes if the user is asleep. In another embodiment of the present invention, the stimulation intensity is reduced by 2 dB if the user is determined to be asleep. In another embodiment of the present invention, the start of the next scheduled session is delayed if the sleep can be characterized as restful (not fragmented) in the recent past. In another embodiment of the present invention, no sessions start after the user is determined to be asleep. Still other adaptive adjustments to the TENS stimulation parameters may be made based on the user's sleep characteristics and the user's potential needs for TENS stimulation therapy to control pain.

In one preferred form of the present invention, there is provided apparatus for providing transcutaneous electrical nerve stimulation (TENS) therapy to a user, said apparatus comprising:

a housing;

an application unit for providing mechanical coupling between said housing and the user's body;

a stimulation unit for electrically stimulating at least one nerve of the user;

a sensing unit for (i) sensing the user's body movement and body orientation to determine whether the user is in an "out-of-bed" state or a "rest-in-bed" state, and (ii) analyzing the sleep characteristics of the user during said "rest-in-bed" state; and a feedback unit for at least one of (i) providing the user with feedback in response to said analysis of said sleep characteristics of the user, and (ii) modifying the electrical stimulation provided to the user by said stimulation unit in response to said analysis of said sleep characteristics of the user;

wherein said sleep characteristics comprise a likelihood measure of the user's sleep quality.

In another preferred form of the present invention, there is provided a method for applying transcutaneous electrical nerve stimulation to a user, said method comprising the steps of:

applying a stimulation unit and a sensing unit to the body of the user;

using said stimulation unit to deliver electrical stimulation to the user so as to stimulate one or more nerves of the user;

analyzing electromechanical sensing data collected by said sensing unit in order to (i) determine the user's body orientation, and (ii) quantify body activity levels so as to determine whether the user is in an "out-of-bed" state or a "rest-in-bed" state, whereby to determine the quality and duration of the user's sleep during the "rest-in-bed" state; and modifying the electrical stimulation delivered by said stimulation unit based on said sleep quality and said duration of the user's sleep during the "rest-in-bed" state.

In another preferred form of the present invention, there is provided apparatus for monitoring the sleep patterns of a user, said apparatus comprising:

a housing;

an application unit for providing mechanical coupling between said housing and the user's body;

a sensing unit carried by the housing for (i) sensing the user's body movement and body orientation to determine whether the user is in an "out-of-bed" state or a "rest-in-bed" state, and (ii) analyzing the sleep characteristics of the user during said "rest-in-bed" state; and a feedback unit for providing the user with feedback in response to said analysis of said sleep characteristics of the user.

In another preferred form of the present invention, there is provided a method for monitoring the sleep patterns of a user, said method comprising of the steps of:

applying a sensing unit and a feedback unit to the body of a user;

using said sensing unit to determine the user's body movement and body orientation to (i) determine whether the user is in an "out-of-bed" state or a "rest-in-bed" state, and (ii) analyze the sleep characteristics of the user during said "rest-in-bed" state; and providing the user with feedback via said feedback unit in response to said analysis of said sleep characteristics of the user.

In another preferred form of the present invention, there is provided apparatus for providing transcutaneous electrical nerve stimulation (TENS) therapy to a user, said apparatus comprising:

a housing;

an application unit for providing mechanical coupling between said housing and the leg of a user;

a stimulation unit for electrically stimulating at least one nerve of the user; and a sensing unit for (i) sensing the user's leg orientation and leg motion to determine whether the user is in an "out-of-bed" state or a "rest-in-bed state", wherein sensing the user's leg orientation comprises determining the user's leg elevation and leg rotation, and further wherein sensing the user's leg motion comprises determining the user's net activity and leg movements, and (ii) analyzing the sleep characteristics of the user during said "rest-in-bed" state; and a controller for modulating said stimulation unit based on said determinations made by said sensing unit.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

The Novel TENS Device in General

Figure 1:
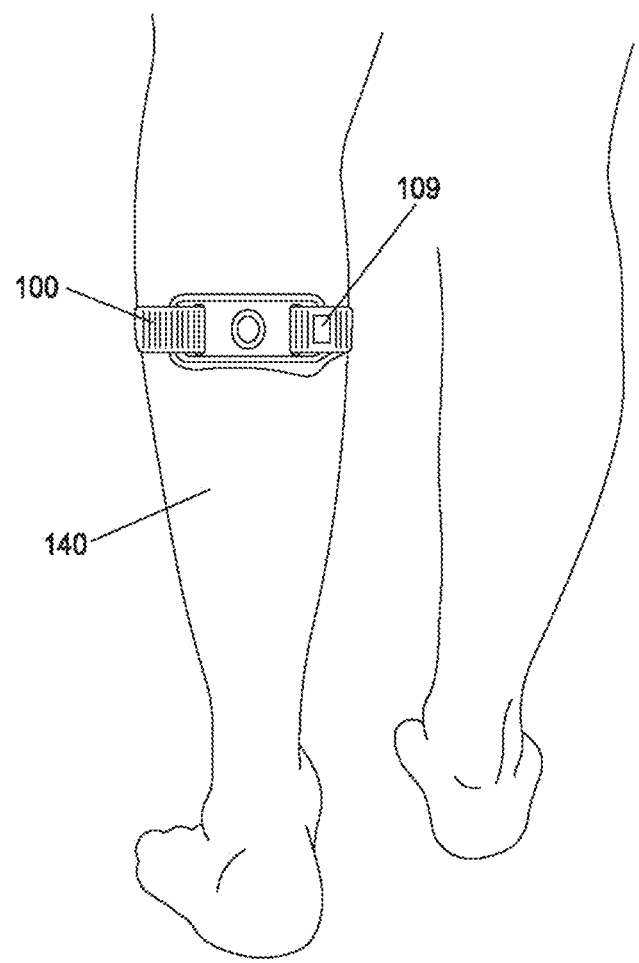
FIG. 1 is a schematic view showing a novel TENS device formed in accordance with the present invention, with the novel TENS device being mounted to the upper calf of a user.

FIG. 1 illustrates a novel TENS device 100 formed in accordance with the present invention, with the novel TENS device being shown worn on a user's upper calf 140. A user may wear TENS device 100 on either leg or a user may wear one TENS device 100 on each leg.

Figure 2:
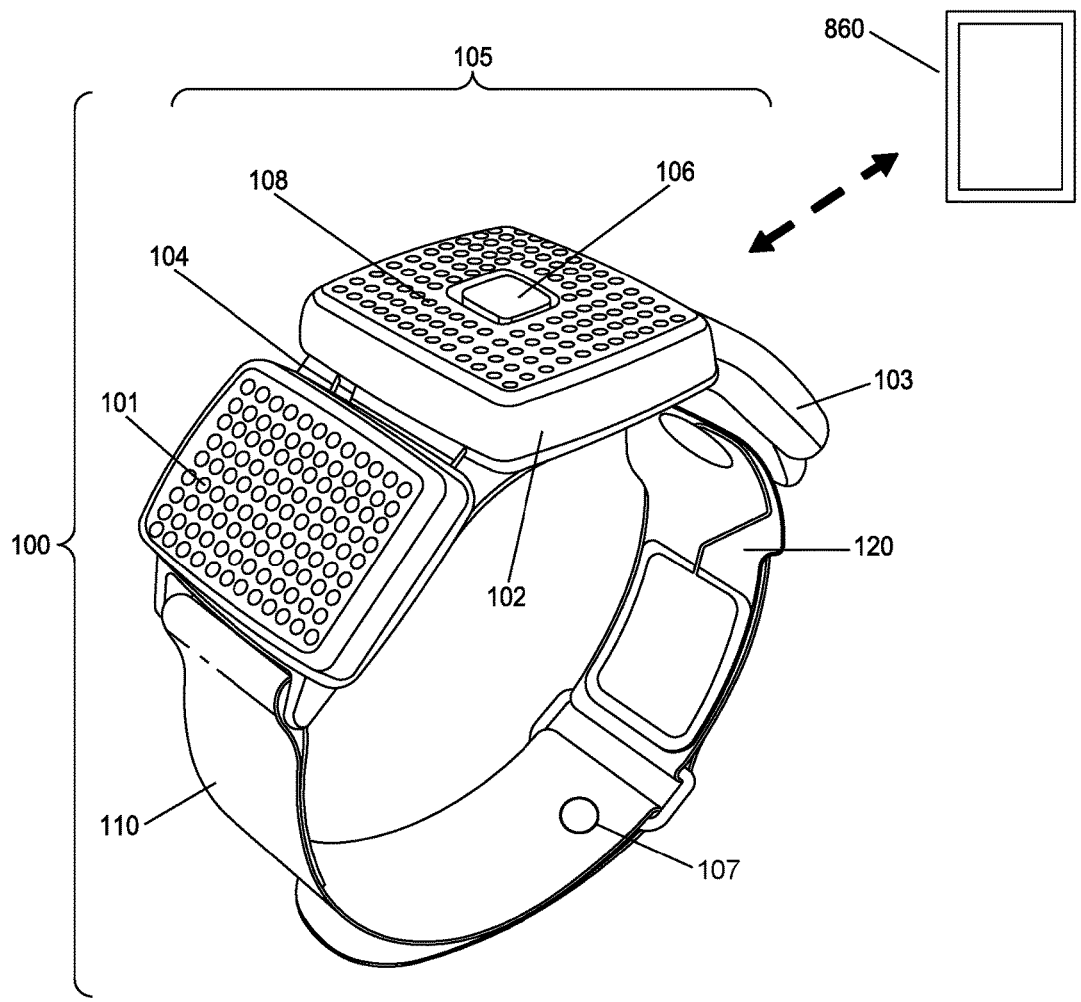
FIG. 2 is a schematic view showing the novel TENS device of FIG. 1 in greater detail.
Figure 4:
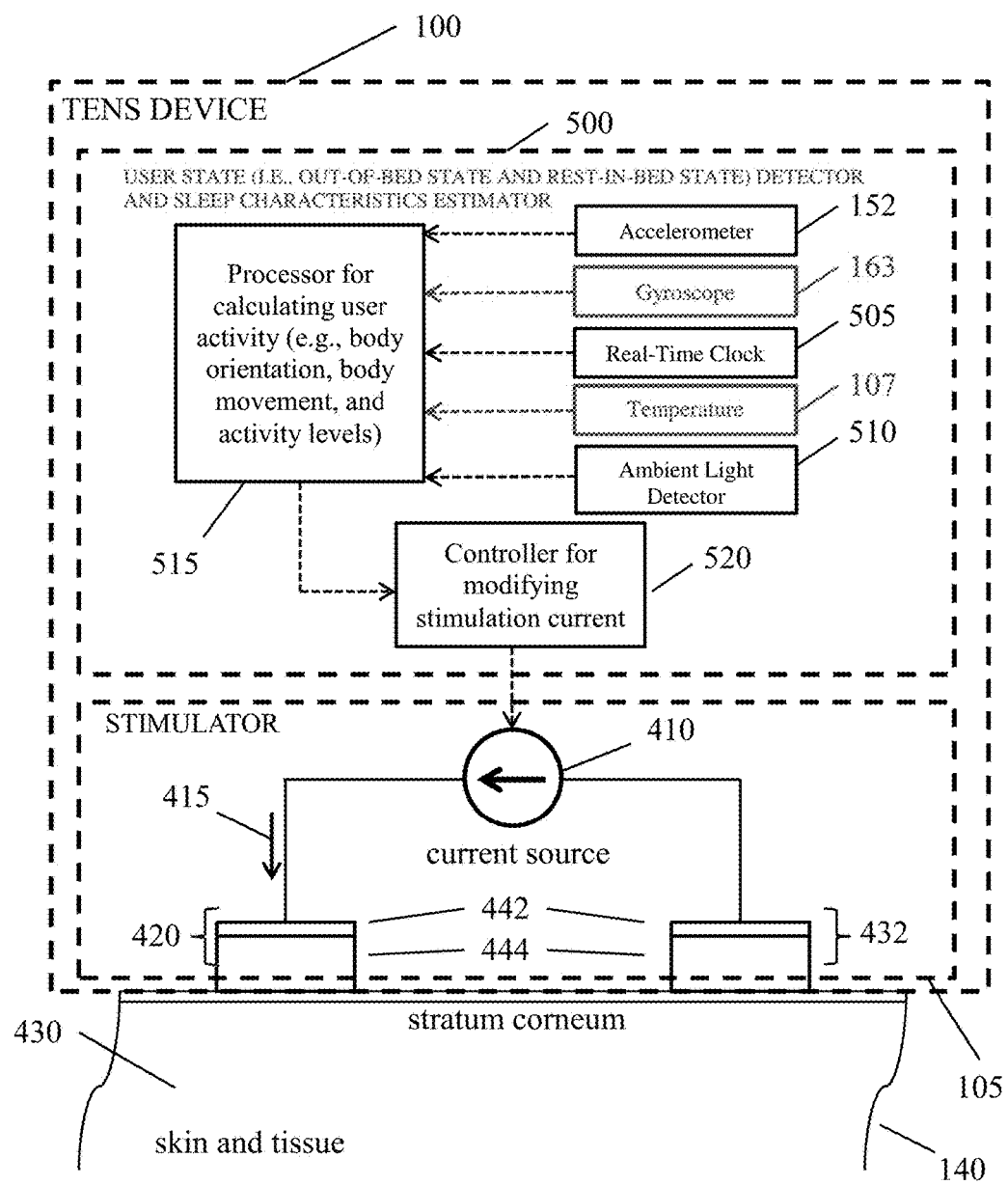
FIG. 4 is a schematic view of the novel TENS device of FIGS. 1 and 2, including its user state (i.e., out-of-bed and rest-in-bed) detector and sleep characteristics estimator.
Figure 6:
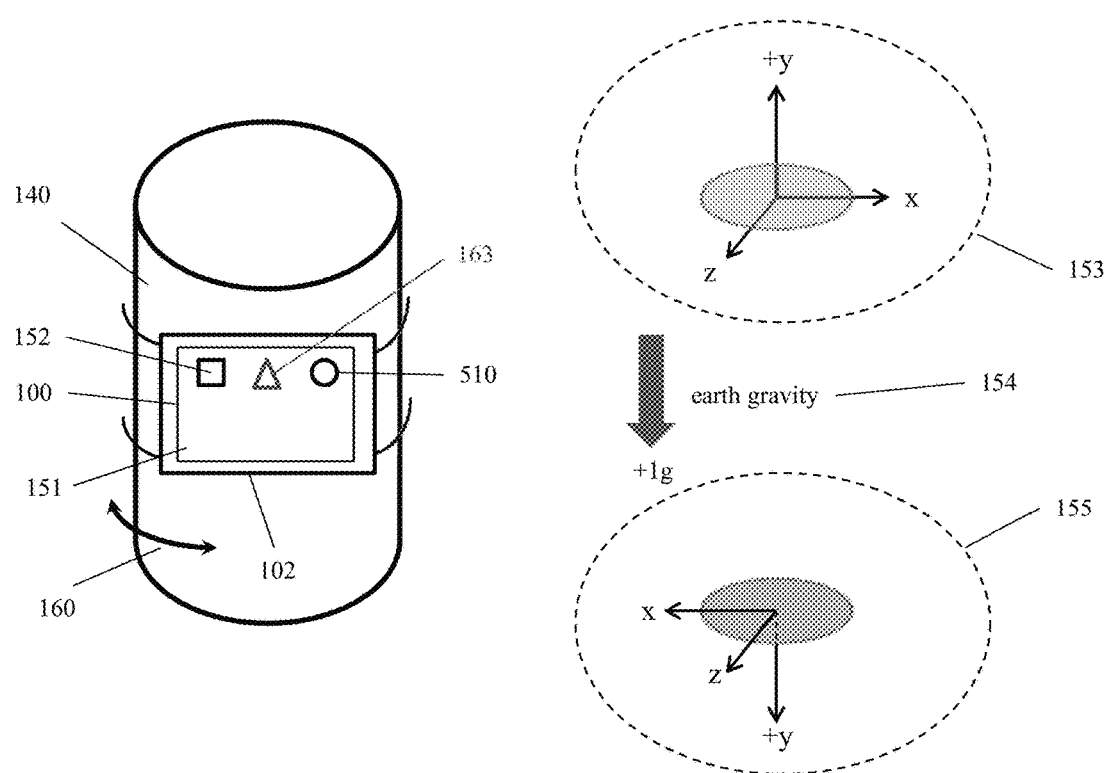
FIG. 6 is a schematic view showing the orientation of the accelerometer incorporated in the novel TENS device of FIGS. 1 and 2, when the novel TENS device of FIG. 1 is applied to the upper calf of a user.

TENS device 100 is shown in greater detail in FIG. 2 and preferably comprises three primary components: a stimulator 105, a strap 110, and an electrode array 120 (comprising a cathode electrode and an anode electrode appropriately connected to stimulator 105 as is well known in the art). Stimulator 105 preferably comprises three mechanically and electrically inter-connected compartments 101, 102, and 103. Compartments 101, 102, 103 are preferably inter-connected by hinge mechanisms 104 (only one of which is shown in FIG. 2), thereby allowing TENS device 100 to conform to the curved anatomy of a user's leg. In a preferred embodiment of the present invention, compartment 102 houses the TENS stimulation circuitry (except for a battery) and user interface elements 106 and 108. Compartment 102 also houses an accelerometer 152 and a gyroscope 163 (see FIG. 4), preferably in the form of a semiconductor chip comprising the accelerometer and gyroscope, for detecting user gestures, user leg and body orientation, and user leg and body motion, as will hereinafter be discussed. Compartment 102 also houses a real-time clock 505 (FIG. 4). In a preferred embodiment, compartments 101 and 103 are smaller, auxiliary compartments that house a battery for powering the TENS stimulation circuitry and other circuitry, and other ancillary elements, such as an ambient light sensor or detector 510 (FIGS. 4 and 6) for determining ambient light conditions, and a wireless interface unit of the sort well known in the art (not shown) for allowing TENS device 100 to wirelessly communicate with other elements (e.g., a hand-held electronic device such as a smartphone 860). In another embodiment of the present invention, only one or two compartments may be used for housing all of the TENS stimulation circuitry, battery, and other ancillary elements of the present invention. In another embodiment of the present invention, a greater number of compartments are used, e.g., to conform better to the body and to improve user comfort. In another embodiment of the present invention, a flexible circuit board is used to distribute the TENS stimulation circuitry and other circuitry more evenly around the leg and thereby reduce bulk.

A temperature sensor 107 (FIG. 2) is embedded in (or attached to) the strap 110 in order to measure the skin temperature of the user and the measured skin temperature is electrically communicated to the stimulator 105. In another embodiment, temperature sensor 107 is housed in compartment 102 (or one of the other compartments 101, 103).

Still looking now at FIG. 2, user interface element 106 preferably comprises a push button for user control of electrical stimulation, and user interface element 108 preferably comprises an LED for indicating stimulation status and for providing other information to the user. Although a single LED is shown, interface element 108 may comprise multiple LEDs of different colors. Additional user interface elements (e.g., an LCD display, audio feedback through a beeper or voice output, haptic devices such as a vibrating motor, etc.) are also contemplated and are within the scope of the present invention.

The preferred embodiment of the present invention is designed to be worn on the upper calf 140 of the user as shown in FIG. 1. TENS device 100, comprising stimulator 105, electrode array 120, and strap 110, is secured to upper calf 140 by placing the apparatus in position and then tightening strap 110. Although the preferred embodiment of the present invention comprises placement of the TENS device on the upper calf of the user, additional anatomical locations (such as above the knee, on the lower back, and on the upper arm) are also contemplated and are also considered to be within the scope of the present invention. In addition, it should also be appreciated that, if desired, multiple TENS devices 100 may be worn by a user simultaneously (e.g., one TENS device 100 on each upper calf 140 of the user, one TENS device 100 on the upper calf 140 of a user and another TENS device 100 on the lower back of the user, etc.).

Figure 3:
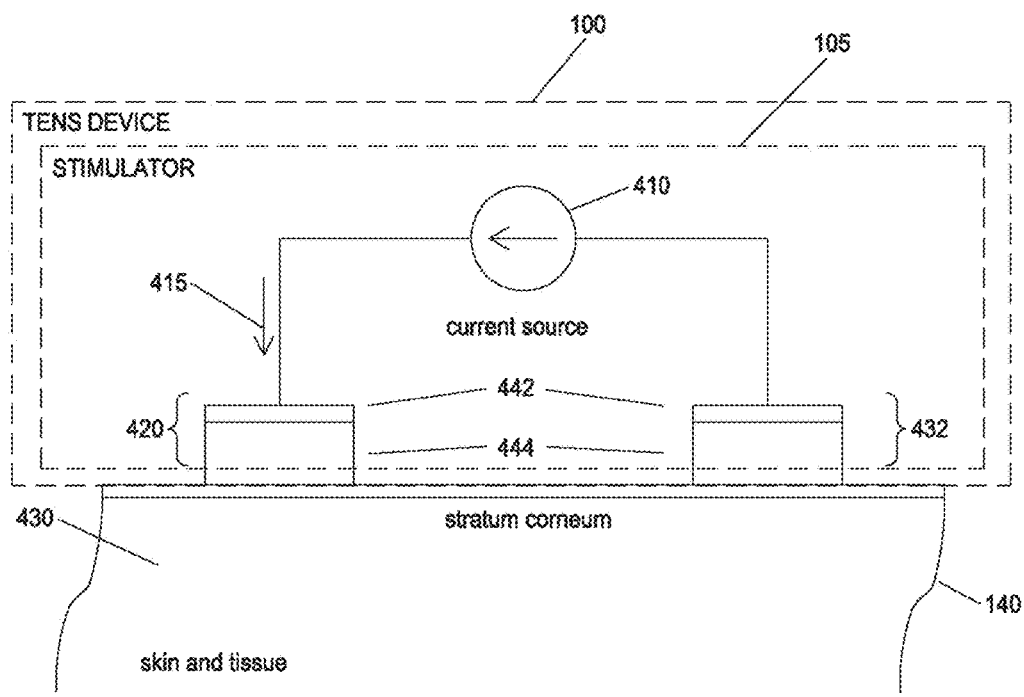
FIG. 3 is a schematic view of the novel TENS device shown in FIGS. 1 and 2 attached to the tissue of a patient.

FIG. 3 is a schematic representation of the current flow between TENS device 100 and the user. As seen in FIG. 3, stimulation current 415 from a constant current source 410 flows into the user's tissue 430 (e.g., the user's upper calf) via anode electrode 420. Anode electrode 420 comprises a conductive backing (e.g., silver hatch) 442 and hydrogel 444. The current passes through the user's tissue 430 and returns to constant current source 410 through cathode electrode 432 (cathode electrode 432 also comprises a conductive backing 442 and hydrogel 444). Constant current source 410 preferably provides an appropriate biphasic waveform (i.e., biphasic stimulation pulses) of the sort well known in the art of TENS therapy. In this respect it should be appreciated that the designation of "anode" and "cathode" electrodes is purely notational in the context of a biphasic waveform (i.e., when the biphasic stimulation pulse reverses its polarity in its second phase of the biphasic TENS stimulation, current will be flowing into the user's body via "cathode" electrode 432 and out of the user's body via "anode" electrode 420).

Further details regarding the construction and use of the foregoing aspects of TENS device 100 are disclosed in (i) U.S. Pat. No. 8,948,876, issued Feb. 3, 2015 to NeuroMetrix, Inc. and Shai N. Gozani et al. for APPARATUS AND METHOD FOR RELIEVING PAIN USING TRANSCUTANEOUS ELECTRICAL NERVE STIMULATION, which patent is hereby incorporated herein by reference, and (ii) prior U.S. patent application Ser. No. 14/230,648, filed Mar. 31, 2014 by Shai N. Gozani et al. for DETECTING CUTANEOUS "ELECTRODE PEELING" USING ELECTRODE-SKIN IMPEDANCE, issued as U.S. Pat. No. 9,474,898 on Oct. 25, 2016, which patent is hereby incorporated herein by reference.

The User State Detector

In accordance with the present invention, TENS device 100 further comprises (e.g., within compartment 102) user state detector 500 for (i) determining the sleep-wake state of the user (i.e., for determining whether a user is in an "out-of-bed" state or a "rest-in-bed" state), (ii) analyzing the sleep of the user, and/or (iii) providing enhanced transcutaneous electrical nerve stimulation (TENS) using the same. To this end, and looking now at FIG. 4, user state detector 500 generally comprises the aforementioned accelerometer 152, the aforementioned gyroscope 163, the aforementioned real-time clock 505, the aforementioned temperature sensor 107, the aforementioned ambient light detector 510, a processor 515 for calculating user activity (e.g., body orientation, body movement and activity levels) and sleep quality, and a controller 520 for modifying the operation of the constant current source 410 of TENS device 100 so as to provide customized and adaptive TENS stimulation in accordance with determinations made by processor 515. It will be appreciated that processor 515 preferably comprises a microprocessor of the sort well known in the art having appropriate software programming for providing the functions herein disclosed. It will also be appreciated that controller 520 preferably comprises a programmable controller of the sort well known in the art for controlling operation of the TENS stimulator as discussed herein.

When the TENS device is secured in position on the user's upper calf, the position and orientation of accelerometer 152 and gyroscope 163 (FIG. 4) of TENS device 100 is fixed relative to the lower limb of the user. Tight mechanical coupling between TENS device 100 and lower limb 140 allows movement of the user's lower limb to be accurately measured by accelerometer 152 and/or gyroscope 163. Such tight mechanical coupling is preferably established through the aforementioned strap 110. Alternatively, tight mechanical coupling may be established through other means, e.g., a flexible band encasing the TENS device. If desired, a tension gauge 109 (FIG. 1) may be provided on strap 110 to confirm that a tight mechanical coupling is established between TENS device 100 and upper calf 140.

Data from accelerometer 152 and gyroscope 163 are analyzed in real time by processor 515 of user state detector 500 to determine the orientation and motion of the lower limb (i.e., upper calf 140) of the user. The orientation, motion, and activity level of the lower limb (i.e., upper calf 140) of the user, determined by analyzing the data from accelerometer 152 and/or gyroscope 163 (or a combination of data from both accelerometer 152 and gyroscope 163), are used to determine the sleep-wake state, sleep patterns, and sleep characteristics of the user. Based on the sleep-wake state, sleep patterns, and sleep characteristics of the user, TENS device 100 can modify its stimulation pattern (such as the stimulation intensity level and the onset of the stimulation) via controller 520, or provide the user with additional feedback (such as mechanical vibration if the duration of the sleep-on-back state exceeds a threshold), or postpone the preprogrammed auto-start of the next TENS therapy session (e.g., if the user is determined to be in a state of "sound sleep" or "sleep without fragmentation"). In another form of this invention, data from gyroscope 163 are used to determine leg orientation and motion, particularly rotational motion, in order to determine the sleep pattern and/or sleep characteristics of the user.

The leg orientation and leg motion components measured by the user state detector 500 of the present invention may individually or collectively contribute to the determination of the sleep-wake state and/or sleep characteristics of the user. In one preferred form of the invention, processor 515 of TENS device 100 measures the calf orientation of the user, which is highly correlated with the body orientation of the user. More particularly, upright body orientation is generally a reliable indicator that the user is in a wake state, while recumbent orientation suggests a resting state (e.g., such as occurs during a sleep or "rest-in-bed" state). Regular and robust body movement is more likely the result of user activities during the daytime (e.g., walking during an "out-of-bed" or "wake" state), while quiet or low-level spontaneous movements are more likely during nighttime (e.g., spontaneous leg movement during a "rest-in-bed" or "sleep" state). Interactions of body orientation and movement level can also be useful in identifying the sleep-wake state of the user (i.e., thereby enhancing a sleep-wake state classification). Specifically, recumbent body orientation and a low-level of physical activity is generally a good indicator that the user is asleep, while a consistent and repeated movement of the user's leg while in an upright orientation is a reliable indicator that the user is out of bed (i.e., in a "wake" state).

In addition, real-time clock 505 of user state detector 500 allows assigning a nontrivial a priori probability of the sleep-wake state at any given time of the day in order to further refine the sleep-wake state classification results obtained by the aforementioned analysis of leg orientation and leg motion data (i.e., a user is more likely to be asleep at 3:00 am and less likely to be asleep at 4:00 pm). In a preferred embodiment of the present invention, to reflect that the a priori probability that the sleep state is low at a specific daytime window (even when the activity and orientation data suggest that the user is in "rest-in-bed" state), the threshold value for classifying user body orientation as recumbent can be made more stringent.

In another embodiment of the present invention, output from ambient light sensor 510 is used to improve sleep-wake classification results. The ambient light sensor 510 can be used to determine if the user is in an environment which has an illuminated or non-illuminated ambience, to reflect the a priori probability that a user is more likely to be sleeping in a dark setting than in a brightly lit setting. Accordingly, the threshold values for classifying user body position and motion level can be adjusted to reflect the a priori probability of sleep.

In another embodiment of the present invention, output from body temperature sensor 107 is used to improve sleep pattern classification results. It has been recognized that body temperature fluctuates with different sleep stages. In particular, body temperature tends to drop after the onset of sleep (i.e., "stage 2" of sleep, when a user is no longer conscious of their surroundings). Incorporating a skin temperature measurement into the sleep monitoring function of TENS device 100 improves the accuracy of the classification of sleep stages and determination of sleep quality made by TENS device 100 (i.e., by processor 515 of TENS device 100).

On-Skin Detector

In one preferred form of the invention, TENS device 100 may comprise an on-skin detector to confirm that TENS device 100 is firmly seated on the skin of the user.

Figure 5:
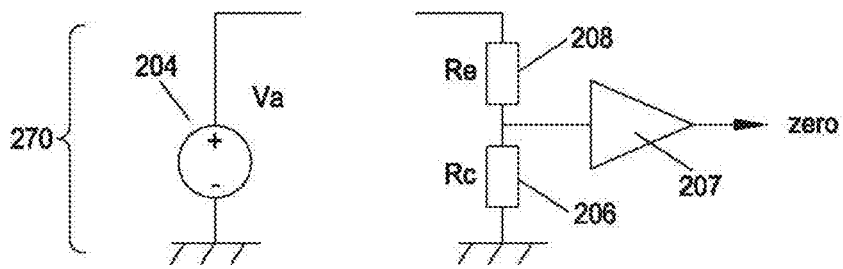
FIG. 5 is a schematic view showing the on-skin detection system of the novel TENS device shown in FIGS. 1 and 2, as well as its equivalent circuits when the novel TENS device is on and off the skin of a user.
Figure 5:
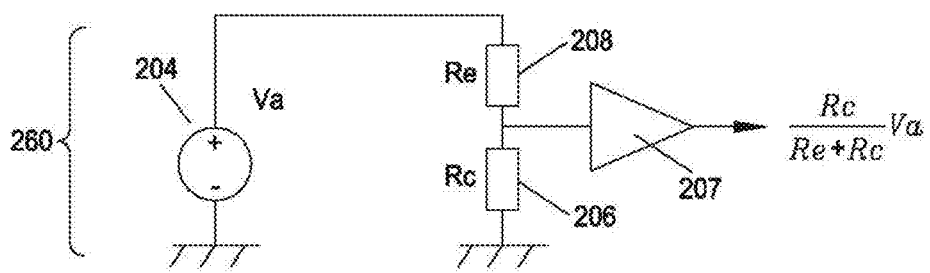
Figure 5:
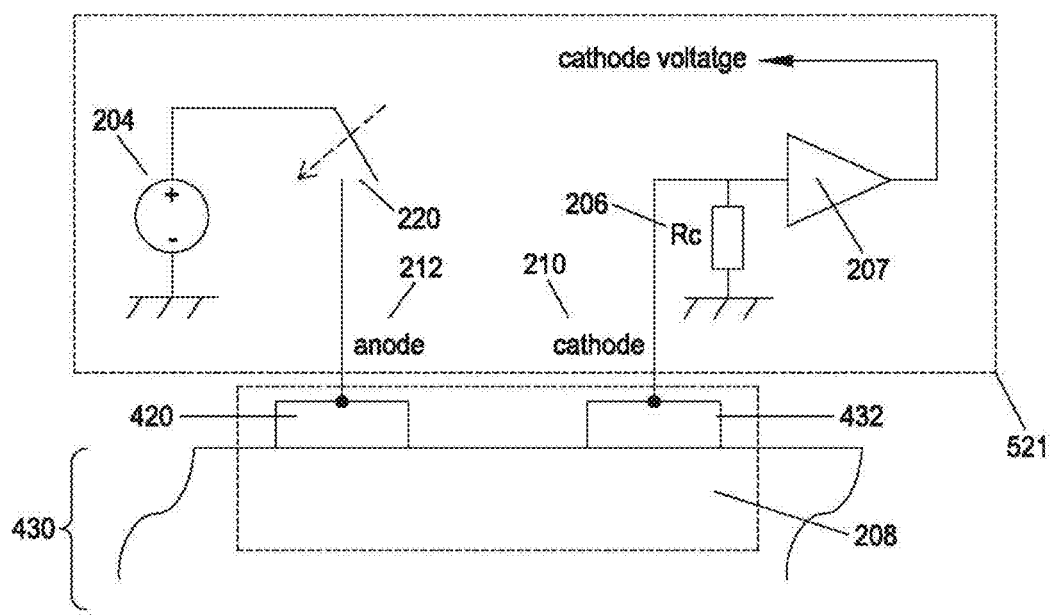

More particularly, the orientation and motion measures from accelerometer 152 and/or gyroscope 163 of TENS device 100 only become coupled with the orientation and motion of a user when the TENS device is worn by the user. In a preferred embodiment, an on-skin detector 521 is provided to determine whether and when TENS device 100 is securely placed on the user's upper calf. In the preferred embodiment, and looking now at FIG. 5, on-skin detector 521 may be provided within TENS device 100. More particularly, in one preferred form of the invention, a voltage of 20 volts from voltage source 204 is applied to the anode terminal 212 of TENS stimulator 105 by closing the switch 220. If the TENS device is worn by the user, then user tissue 430, interposed between anode electrode 420 and cathode electrode 432, will form a closed circuit to apply the voltage to the voltage divider circuit formed by resistors 208 and 206. More particularly, when TENS device 100 is on the skin of the user, the equivalent circuit 260 shown in FIG. 5 represents the real-world system and equivalent circuit 260 allows the anode voltage $V_a$ 204 to be sensed through the voltage divider resistors 206 and 208. The cathode voltage measured from the amplifier 207 will be non-zero and close to the anode voltage 204. On the other hand, when TENS device 100 is not on the skin of the user, the equivalent circuit 270 represents the real-world system and the cathode voltage from amplifier 207 will be zero.

On-skin detector 521 is preferably employed in two ways.

First, if on-skin detector 521 indicates that electrode array 120 of TENS device 100 has become partially or fully detached from the skin of the user, TENS device 100 can stop applying TENS therapy to the user.

Second, if on-skin detector 521 indicates that electrode array 120 of TENS device 100 has become partially or fully detached from the skin of the user, processor 515 of TENS device 100 will recognize that the data from accelerometer 152 and/or gyroscope 163 may not reliably reflect user leg orientation and leg motion, and user state detector 500 can take appropriate action (e.g., alert the user). In this respect it should be appreciated that, when the on-skin detector 521 indicates that TENS device 100 is on the skin of the user, and accelerometer 152 and/or gyroscope 163 is closely coupled to the lower limb of the user, the data from accelerometer 152 and/or gyroscope 163 may be representative of user leg orientation and user leg motion. However, when the on-skin detector 521 indicates that TENS device 100 is not on the skin of the user, accelerometer 152 and/or gyroscope 163 is not closely coupled to the lower limb of the user, and the data from accelerometer 152 and/or gyroscope 163 will not be representative of user leg orientation and user leg motion.

Electromechanical Sensor Data Processing

In one preferred form of the invention, user state detector 500 comprises a processor 515 for taking the accelerometer data from accelerometer 152 and calculating user activity (e.g., body orientation, body movement and activity levels). In another form of the invention, data from gyroscope 163 are used by processor 515 to calculate user activity. In another form of the invention, data from both accelerometer 152 and gyroscope 163 are combined and used by processor 515 in order to calculate user activity and body orientation, especially transitions in body orientation from one position to another position.

More particularly, in one preferred form of the invention, processor 515 uses the accelerometer data from accelerometer 152 and/or data from gyroscope 163 to measure the user's leg orientation, which is highly correlated with body orientation and therefore indicative of the user's recumbent state (and therefore the user's "rest-in-bed" state); and processor 515 uses the accelerometer data from accelerometer 152 to measure the user's leg motion, which is also indicative of the user's sleep-wake state and leg motion activity levels; and processor 515 uses the determinations of user leg orientation and user leg motion to enhance sleep characterization accuracy.

More particularly, processor 515 uses the accelerometer data from accelerometer 152 to measure two distinct aspects of the user's leg orientation: leg "elevation" (or the angle of the lower leg relative to the horizontal plane), and leg "rotation" (or the angle of rotation of the lower leg about its own axis). Measurement data provided to processor 515 from gyroscope 163 are especially useful in detecting and quantifying angular rotation of the user's leg about the axis of the user's leg.

And processor 515 uses the accelerometer data from accelerometer 152 to measure two distinct aspects of leg motion: "net activity" (which is the magnitude of movement-related acceleration averaged within one-minute windows), and "leg movements" (or brief events that are known to occur in sleep but are not evident in net activity). Some leg movements accompanied by a large leg rotation may be further classified as "body roll events" (such as occur when rolling over in bed).

Raw Data Stream at 50 Hz and 10 Hz.

In a preferred embodiment of the present invention, processor 515 for calculating user activity (e.g., body orientation, body movement and activity levels) is constructed and configured to operate as follows. Raw accelerometer data produced at 400 Hz are decimated to 50 Hz. Following that, the time scale of an "instant" is defined to be equal to 0.1 sec. The 50 Hz data on each axis (x, y, z) are separately averaged over each instant, to provide a low-noise data stream at 10 Hz, denoted by $A_x(t)$, $A_y(t)$, and $A_z(t)$.

Orientation Data Stream.

The accelerometer data $A_x(t)$, $A_y(t)$, and $A_z(t)$ are used to form features which are averages of $A_x(t)$, $A_y(t)$, and $A_z(t)$ over a longer time window (e.g., a one minute window) to capture the steady-state projection of earth gravity along each axis (x, y, z). These features are used for detecting leg orientation (i.e., leg elevation and leg rotation).

Activity Data Stream.

Additionally, the accelerometer data $A_x(t)$, $A_y(t)$, and $A_z(t)$ are high-pass filtered to remove the static gravity component in order to isolate acceleration components caused by leg movement. The high-pass filter has −3 dB point at 0.5 Hz. High-pass filtered accelerometer data are denoted as $\tilde{A}_x(t)$, $\tilde{A}_y(t)$, and $\tilde{A}_z(t)$.

Data from the gyroscope 163 are processed similarly to produce data streams with difference sampling rates.

Leg Elevation Detection

In one preferred form of the invention, user state detector 500 is configured to detect leg elevation.

More particularly, in order to determine the "body orientation state" for the purpose of sleep monitoring, the present invention uses the leg elevation, which is computed by processor 515 of user state detector 500, based on measurement data from accelerometer 152 and/or gyroscope 163 when TENS device 100 is placed on the user's upper calf 140 (FIG. 1). In a preferred embodiment, and looking now at FIG. 6, accelerometer 152 (and/or gyroscope 163) is located on the circuit board 151 of the TENS circuitry housed inside compartment 102, so that the accelerometer's 3-axis directions, shown at 153 in FIG. 6 (i.e., x-axis, y-axis, z-axis), are known and fixed in relationship to the lower leg when the TENS device is placed on the user's upper calf: the y-axis is aligned longitudinally along the longitudinal axis of the lower leg; the x-axis is disposed tangential to the surface of the lower leg and perpendicular to the y-axis, and the z-axis points radially away from the surface of the lower leg.

A stationary upright user, or one sitting with feet resting on the ground, will have an upright calf elevation. Consequently, the y-axis acceleration of accelerometer 152 will have a value of about −1 g due to Earth gravity 154 (FIG. 6), where g is the acceleration due to Earth gravity. The above measurement holds true regardless of the exact rotational position 160 of compartment 102 around upper calf 140. When TENS device 100 is placed upside down on the upper calf, which is a possible placement position, the accelerometer axes rotate as shown at 155 in FIG. 6. In this case, a stationary upright user will have a measured acceleration value along the y-axis of about +1 g. By contrast, a stationary recumbent user lying with legs elevated on a bed will have a measured acceleration value along the y-axis of about 0 g. In a preferred embodiment, if the absolute value of the y-axis acceleration measurement is greater than a threshold level, then the leg elevation is considered to be upright, otherwise the leg elevation is considered to be recumbent.

Figure 7:
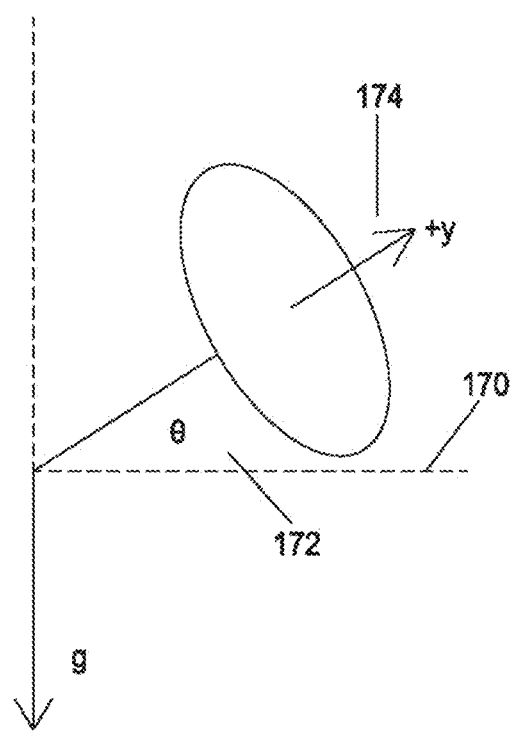
FIG. 7 is a schematic view showing the relationship between gravitational force vector g and the accelerometer y-axis in the novel TENS device when the novel TENS device (applied to upper calf of the user) rests at an elevation angle θ with respect to the horizontal plane.

Looking now at FIG. 7, where the Earth's gravitational vector is downward, the elevation angle θ (172) represents the angle between the positive accelerometer y-axis direction (174) and the true horizontal plane (170). In a preferred embodiment, the y-axis acceleration measurement threshold level is set to 0.50 g, corresponding to a leg elevation angle θ≈30° from the horizontal plane, however, other threshold values may also be used, and users may have the option of adjusting this value to better distinguish their sleep and wake behaviors.

In general, the acceleration measured along the y-axis will include not only the projection of gravity onto that axis, but also a contribution from motion:

$$A_y(t) = \pm \sin|\theta(t)| + m(t) \text{[in unit of g]}$$

where t is time, and m(t) is the contribution due to leg motion. The specific ±sign depends upon the TENS device placement on upper calf 140 and is fixed for each placement. The motion component m(t) is considered "noise" in the context of determining leg elevation, and will have zero mean over a sufficiently large window.

In a preferred embodiment, a leg elevation algorithm, taking into account user body movement, is implemented by processor 515 of user state detector 500 (i.e., to determine whether the user is in an "out-of-bed" state when the user is upright or whether the user is in a "rest-in-bed" state when the user is recumbent) in the following manner.

Figure 10:
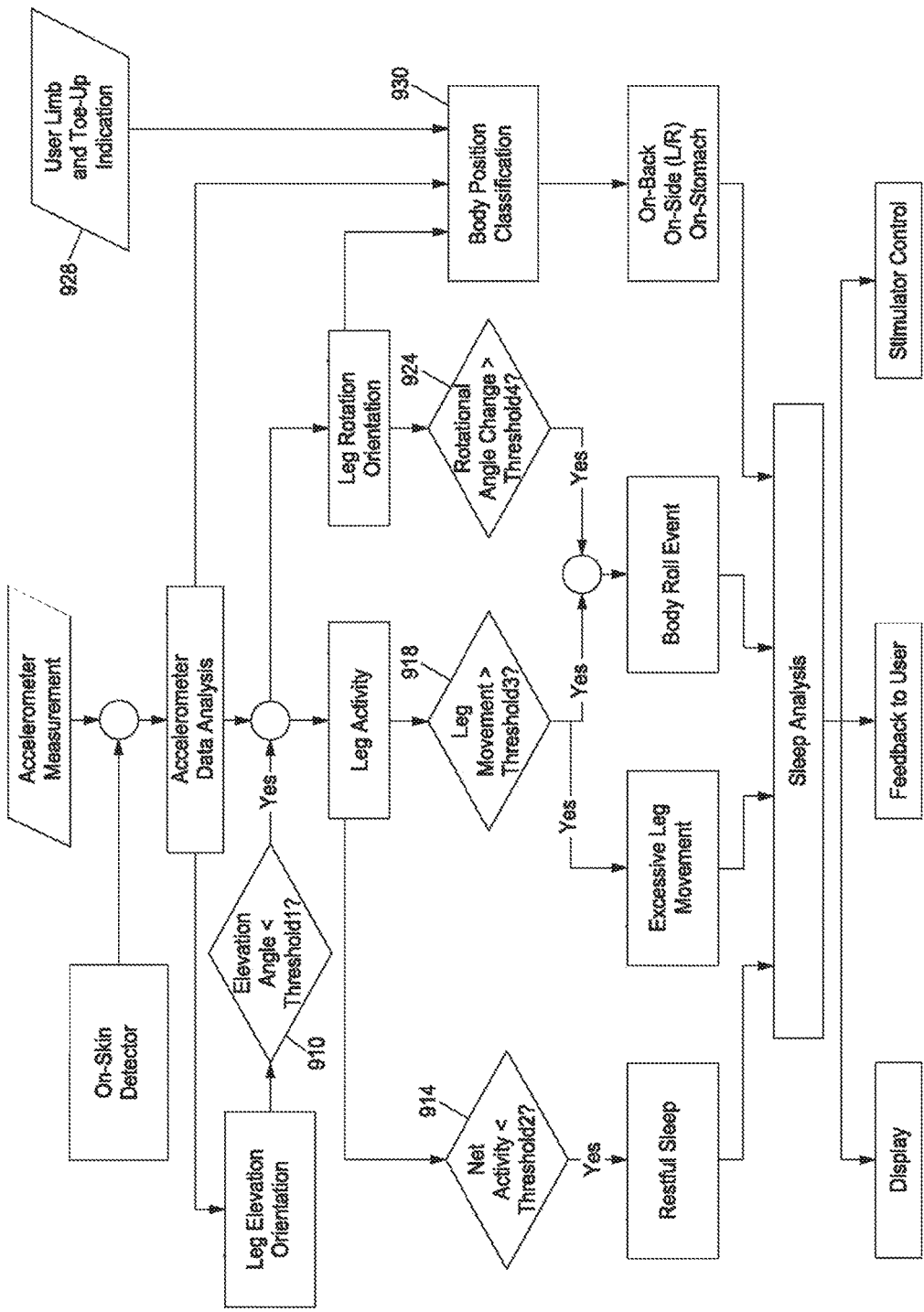
FIG. 10 is a schematic flow chart showing exemplary operation of the novel TENS device, including its user state detector.

Step 1. Set a target angle threshold $\theta_0$ (this is the "Threshold1" shown at step 910 in FIG. 10) for the angle θ so that $|\theta|<\theta_0$ corresponds to the case where the upper calf 140 of the user is recumbent. In a preferred embodiment, the target angle threshold $\theta_0$ is set to 30°.

Step 2. Define non-overlapping windows of length N, called "epochs". The time at the end of each epoch is denoted T. In a preferred embodiment, the accelerometer data (in units of g, standard earth gravity) are segmented into epochs, i.e., one-minute windows. With an accelerometer data rate of 10 Hz, the epoch length is N=600. The mean $A_{y,T}$ and the standard error of the mean $SE_{y,T}$ are calculated based on samples in each epoch.

Step 3. Let $\theta_T = \sin^{-1} A_{y,T}$. Values of $\theta_T \approx \theta_0$ can lead to erratic switching of the leg elevation state. In order to reduce this, define a hysteresis band $\theta_0 \pm \theta_H$. In the preferred embodiment, the hysteresis parameter $\theta_H$ is set to 2.5°, but other values are possible (but should be small compared to $\theta_0$). In the preferred embodiment, rather than computing $\sin^{-1}$ for every epoch, the angular thresholds are instead converted to acceleration units, i.e., by computing two thresholds $A_\pm = \sin(\theta_0 \pm \theta_H)$, against which $A_{y,T}$ will be compared.

Step 4. The ability of the hysteresis band to prevent erratic switching of the leg elevation state depends upon the amount of noise in the data, characterized by $SE_{y,T}$, which is the standard error of the mean $A_{y,T}$. In order to account for the noise level in the data, processor 515 of user state (i.e., leg orientation and leg motion) detector 500, processor 515 compares the acceleration data $A_{y,T}$ to the thresholds $A_\pm$. However, instead of comparing the mean $A_{y,T}$ per se to the thresholds $A_\pm$, processor 515 compares the "confidence interval" $A_{y,T} \pm \eta SE_{y,T}$ to the thresholds $A_\pm$. More specifically, for each epoch, if the prior elevation state was recumbent, in order to classify the next state as upright, processor 515 of user state detector 500 requires $[|A_{y,T}| - \eta SE_{y,T}] > A_+$. If the prior elevation state was upright, in order to classify the next state as recumbent, processor 515 of user state detector 500 requires $[|A_{y,T}| + \eta SE_{y,T}] < A_-$. In a preferred embodiment η=3, but other values are possible.

It should be appreciated that the hysteresis band is helpful as described above, but in another form of the invention the hysteresis band is omitted, which is the same as setting its band $\theta_H$ to 0°.

Instantaneous Activity

In one preferred form of the invention, processor 515 of user state detector 500 may be configured to detect instantaneous activity.

More particularly, when TENS device 100 is worn on the user's upper calf 140, the user's activity will be captured by accelerometer 152 of the TENS device. Each axis (x, y, z) of accelerometer 152 measures the projection of the acceleration vector along that axis. As described above, the measured acceleration includes the static effect of earth gravity, as well as contributions from leg movement. In order to isolate the contributions from leg movement, processor 515 of user state (i.e., leg orientation and leg motion) detector 500 high-pass filters the instant data vector $A(t)=[A_x(t), A_y(t), A_z(t)]$ before further processing.

Although the acceleration component for each individual axis of the accelerometer contains unique and useful information for body movement analysis, the vector magnitude of acceleration, called the "instantaneous acceleration", denoted $\tilde{A}_I(t)$ and defined in equation below, is commonly used to quantify the overall motion-related activity:

$$\tilde{A}_I(t) = \sqrt{\tilde{A}_X(t)^2 + \tilde{A}_Y(t)^2 + \tilde{A}_Z(t)^2}$$

In a preferred embodiment of the present invention, processor 515 of user state detector 500 uses this instantaneous acceleration $\tilde{A}_I(t)$ for the actigraphy calculations. However, calculations based on other combinations of acceleration axes may also be used. For example, rather than combining all three axes equally as done with $\tilde{A}_I(t)$ as defined above, only some axes may be used, or certain axes may be contrasted through subtraction.

In another form of the invention, the y-axis acceleration data $A_y(t)$ is analyzed to detect periodic patterns of movement that match walking activity patterns in order to determine if the user is walking. In yet another form of the invention, data from gyroscope 163 (instead of, or in addition to, data from accelerometer 152) are used to detect periodic patterns of movement that match walking activity patterns in order to determine if the user is walking, since the angular rotation of the user's leg with respect to the user's knee joint generally follows a periodic pattern when the user is walking.

Leg Movement Detector

In one preferred form of the invention, processor 515 of user state detector 500 may be configured to detect leg movement which is more likely to occur during sleep when the user is determined to be in a "rest-in-bed" state.

More particularly, the instantaneous acceleration $\tilde{A}_I(t)$ is a time series comprised of brief events, such as leg movements known to occur during normal and abnormal sleep, and sustained activity, such as occurs during walking, running, or climbing stairs. In a preferred embodiment, leg movements (LM) are computed in a manner that is consistent with the detection of periodic leg movements (PLM) defined in the clinical literature (Bonnet et al, 1993; Zucconi et al, 2006), however, other approaches to detecting brief leg movements are possible and are considered to be within the scope of the present invention.

In the preferred embodiment, a leg movement (LM) detection algorithm is implemented by processor 515 of user state detector 500 in the following manner.

Step 1. Define two thresholds (these are the "Threshold2" and "Threshold3" shown at steps 914 and 918, respectively, in FIG. 10) that through data analysis are found to be sensitive and specific to brief leg movements. In the preferred embodiment, and appropriate to the variance properties of the data measured by the accelerometer 152, these thresholds are 0.02 g (816 in FIG. 8) and 0.03 g (815 in FIG. 8), but other values may also be used.

Step 2. Define an instantaneous activity state (IAS) and initialize the IAS to False.

Step 3. Compute instantaneous acceleration $\tilde{A}_I(t)$ for each time instant.

Step 3. Update the IAS for each time instant as follows. If IAS=False and $\tilde{A}_I(t) > 0.03$ g, then set IAS=True. If IAS=True and $\tilde{A}_I(t) < 0.02$ g, then set IAS=False. Two thresholds used in this way implement hysteresis in a simple way to prevent rapid switching in the IAS.

Step 4. When IAS becomes True, a leg movement (LM) period begins. When IAS becomes false and remains false for more than 0.5 second, the LM period ends. Thus a contiguous time interval in which IAS=True, and surrounded by intervals in which IAS=False, comprises a leg movement (LM) period. However, if contiguous intervals for which IAS is True are separated by less than 0.5 second, the brief interval for which IAS was False is ignored.

Figure 8:
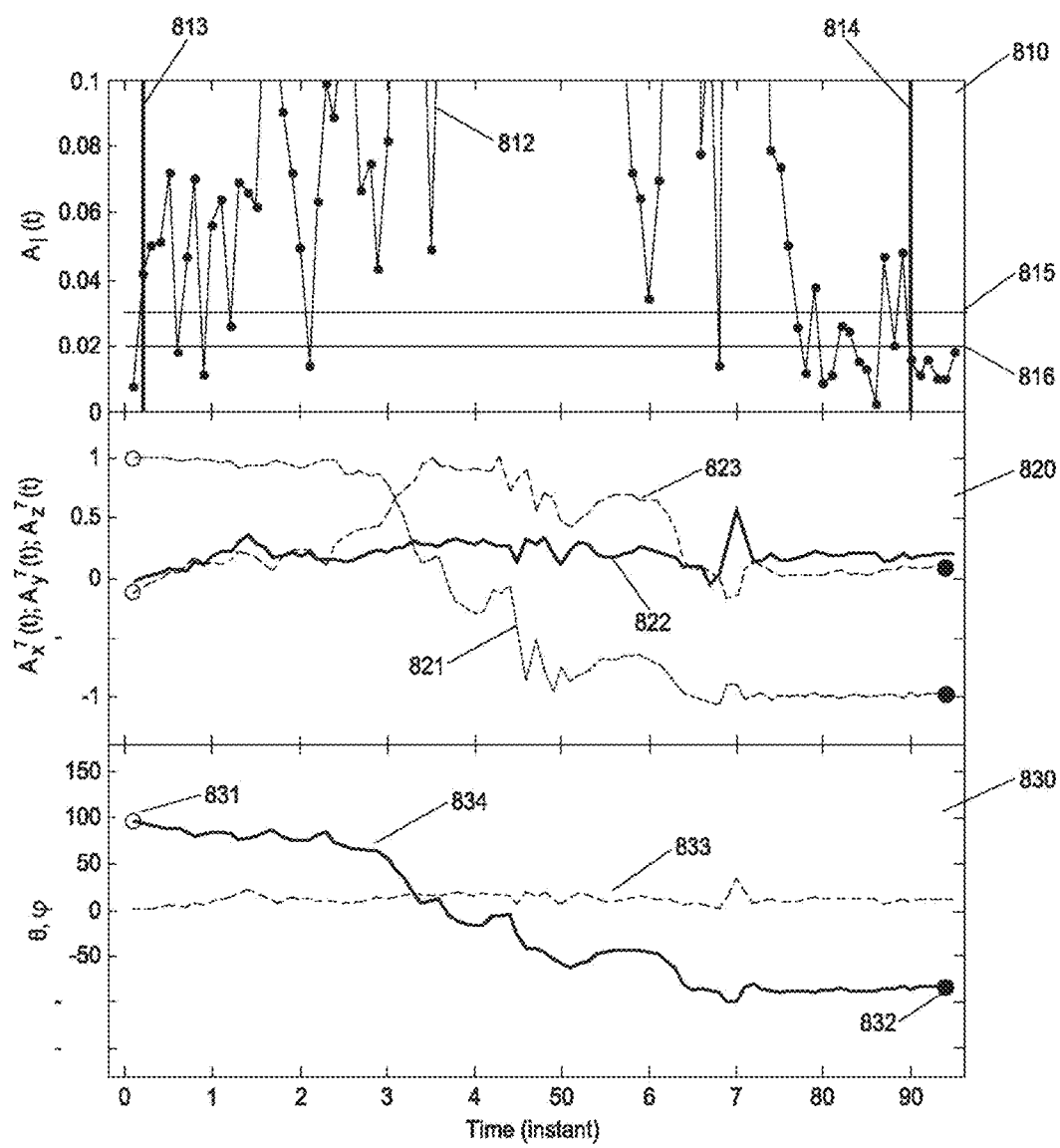
FIG. 8 is a schematic view showing the detection of a leg movement (LM) event, and calculation of the change Δφ in device rotational angle φ after (vs. before) the LM event.

The top panel (810) in FIG. 8 shows an example of the leg movement (LM) detection algorithm applied to real data. Time is measured in instants, i.e., steps of 0.1 second. The dots, and the line 812 connecting them, are the instantaneous accelerations $\tilde{A}_I(t)$. The vertical line 813 is when $\tilde{A}_I(t)$ first went above the threshold 815 (threshold value=0.03 g), at which point IAS was set to True. The instantaneous accelerations $\tilde{A}_I(t)$ fell below the second threshold 816 (threshold value=0.02 g) before the 90$^{th}$ instant. However, their durations were shorter than 0.5 second so they were ignored and the LM period continued. The vertical line 814 shows the instant when $\tilde{A}_I(t)$ first went below the second threshold 816 for more than 0.5 second so the LM period was terminated. The net result is an LM period with a duration of 89 instants (i.e., 8.9 seconds).

Body Roll Detector

In one preferred form of the invention, processor 515 of user state detector 500 is configured to function as a body roll detector when TENS device 100 determines that the user is in a "rest-in-bed" state.

More particularly, when the TENS device 100 (FIG. 9) is worn on the lower leg (i.e., upper calf 140) of a user, its accelerometer 152 will sense the projection of the gravity in its x-z plane when the user is in a recumbent position. The angle φ between the device x-axis and the gravity vector −g can be calculated based on the projected gravity value in the x and z axis. Axis z' is aligned with the "big toe" direction of the user's leg to which the TENS device 100 is attached. Angle α between the device z-axis and the leg x'-axis is fixed when the TENS device is securely placed on the lower leg (i.e., upper calf 140) of the user. Finally, the body orientation angle β defines the relative rotational position between the leg (defined as the direction in which the big toe is pointed, i.e., the z'-axis) and the earth gravity (z"-axis). The angular value remains the same when measuring from the x'-axis to the x"-axis. It is straightforward to derive the relationship between β and φ as follows:

$$\beta = 180 - \alpha - \varphi$$

Because the angle α is fixed, the leg rotation angle β can be derived from the angle φ as measured by the accelerometer 152.

Some brief increases in activity that are classified as leg movement (LM) are associated with large changes in the rotational angle φ measured by the TENS device 100. Rolls of sufficient magnitude are unlikely to involve only the leg, but rather are likely to indicate that the entire body is rolling over while in bed, e.g., from the left side to the right side, or from the back to the left side or the right side. Some leg movements (LMs) may therefore be classified as "body roll events".

In one preferred embodiment, a body roll detection algorithm is implemented by processor 515 in user state detector 500, using only the angle change $\Delta\varphi$, in the following manner:

Step 1. For each LM period detected, select the raw acceleration vector A(t) in short windows before and after the leg movement. In a present invention, this window is an instant (0.1 seconds).

Step 2. Before and after each LM period, take the instant values of A(t) (not high-pass filtered) on each axis separately so as to obtain $A_x(t)$, $A_y(t)$, and $A_z(t)$.

Step 3. Using these values before and after the LM, compute the rotation angle $\varphi$ (t)=a tan 2$\{A_x(t), A_z(t)\}$. The inverse tangent function a tan 2 returns an angle in the range $-180°<\varphi(t)\leq 180°$), i.e., a result in all four possible quadrants.

Step 4. Compute the change in rotational angle $\Delta\varphi=\varphi_{after}-\varphi_{before}$. In order to facilitate comparison with a threshold (this is the "Threshold4" shown at step 924 in FIG. 10), this difference is put in the range $-180°<\Delta\varphi\leq 180°$, i.e., if $\Delta\varphi>180°$ then subtract 360°, but if $\Delta\varphi\leq-180°$ then add 360°.

Step 5. Compare the absolute value $|\Delta\varphi|$ with a threshold value. In the present invention, this threshold value is 50°, but other values may be used. If $|\Delta\varphi|>50°$, then classify the LM event as a "body roll event".

The middle panel (820) in FIG. 8 shows this body roll detection algorithm applied to real data. The acceleration values $A_x(t)$, $A_y(t)$, and $A_z(t)$ are plotted in traces 821, 822, and 823. The y-axis component $A_y(t)\approx 0$ g throughout the event, consistent with the condition that lower leg elevation is in recumbent state. In contrast, $A_x(t)$ and $A_z(t)$ show significant activities, especially between time instants 30 and 70. In addition, the steady state value for $A_x(t)$ changed from +1 g (before the LM period) to −1 g (after the LM period), suggesting a body roll event.

The bottom panel (830) of FIG. 8 shows the calculation of the elevation angle $\theta$ (833) and the rotation angle $\varphi$ (834) for each instant. The elevation angle $\theta\approx 0$ throughout the event, consistent with the lower leg being in recumbent elevation. In contrast, the rotation angle $\varphi$ changes from $\varphi\approx+90°$ (indicated by the empty circle 831) to $\varphi\approx-88°$ (indicated by the filled circle 832). The angular change is $\Delta\varphi\approx 178°$, consistent with a (rightward) roll of the entire body.

These body rolls may be reported directly to the user to inform them about their sleep patterns. In addition, because body roll events may be brief, the associated increase in activity may not be evident in the epoch average of activity, and therefore may not cause that epoch to be classified as awake. Although rolling over in bed may not indicate an awake state, it does indicate momentarily restless sleep. This novel approach for detecting body rolls by evaluating changes in roll angles associated with brief leg movement (LM) permits the differentiation of leg movement associated with no body rolls from leg movement associated with body rolls, and thus provides a finer description of sleep patterns that are useful to the user and their healthcare providers.

In another preferred embodiment, rather than using single instants of A(t) before and after the LM to compute the angles $\varphi$, the mean or median values of A(t) over several instants before and after the LM are used to improve robustness to noise.

In another preferred embodiment, a body roll detection algorithm is implemented by processor 515 of user state detector 500 using the angle change $\Delta\beta$ in the following manner. Consider a person lying on their back, with the TENS device placed on their right leg. Recalling that, with the TENS device placed on either leg, $\beta=0$ when the toes are pointed vertically upward, and $\beta$ increases with counter-clockwise (CCW) rotation, therefore the most likely range of leg rotational positions is $-80°\leq\beta\leq 0°$. Any change in angle $\Delta\beta$ that remains within that range may not likely be associated with a body roll. In contrast, a change in angle $\Delta\beta$ from inside that range to outside that range is most likely associated with a body roll. In this way, using the change in angle $\Delta\beta$, the threshold for detecting a body roll may be adjusted depending upon the leg on which the device is placed. That is to say, in addition to the magnitude of the change $\Delta\beta$, the value of the leg rotation angle $\beta$ before and after the leg movement (LM), and the sign of the angle change $\Delta\beta$ across the leg movement (LM), may be used to improve performance of the body roll detector.

While analyses of accelerometer data based on earth gravity projection provide the steady state value of the rotational angles, it should be appreciated that gyroscope measurements (i.e., data from gyroscope 163) capture transient rotational activities such as angular acceleration and angular velocity. Processing of angular velocity data of the leg (e.g., via processor 515 of user state detector 500 of TENS device 100) allows changes in the leg rotation angle $\beta$ to be directly determined. In one preferred form of the invention, rotational angle changes derived from measurements (i.e., data) collected by gyroscope 163 can be used to detect and quantify a user's leg rotation events. In another form of the invention, data from accelerometer 152 and data from gyroscope 163 are combined together and processed by processor 515 of user state detector 500 of TENS device 100 in order to improve the performance of the body roll detector.

Static Body Rotational Position Detector

In one preferred form of the invention, processor 515 of user state detector 500 may be configured to function as a static body rotational position detector.

More particularly, users with sleep apnea are recommended to sleep not on their back.

Because of the limited rotational range of motion of the human hip, leg rotational position is highly correlated with body position, e.g., when sleeping on one's back, the toes of either foot are pointed upward above the horizontal plane to varying degrees, not likely exactly on the horizontal plane, and never below the horizontal plane. This observation, together with the placement of the novel TENS device on the upper calf of the user, allows an innovative addition to sleep analysis.

The time scale of an "epoch" equal to one minute, and the epoch-averaged non-high-pass filtered acceleration values $\overline{A}_{X,T}(t)$, $\overline{A}_{Y,T}(t)$, and $\overline{A}_{Z,T}(t)$ were introduced above in the section entitled "Leg Elevation Detection". Because it is sufficient to report the time spent sleeping on the back at the resolution of one minute, these epoch-averaged acceleration values may be advantageously used in the following manner to detect static body rotational position.

Consistent with the roll detector definition of the rotational position angle $\varphi$, let $\varphi_T$=a tan 2$\{\overline{A}_{X,T}(t), \overline{A}_{Z,T}(t)\}$ as before, where $\overline{A}_{X,T}(t)$ and $\overline{A}_{Z,T}(t)$ are raw (i.e., not high-pass filtered) accelerations averaged over an epoch T. Let $\beta_T$=the angle of the toes relative to the vertical. The relation between $\varphi_T$ and $\beta_T$ depends upon the rotational placement of the TENS device on the upper calf of the user, denoted $\alpha$. Because the electrode gel 444 is sticky and the strap 110 is supportive, the TENS device does not move on the user's leg once it is placed onto the upper calf 140, therefore the angle $\alpha$ is constant as long as the TENS device is on the leg of the user.

Figure 9:
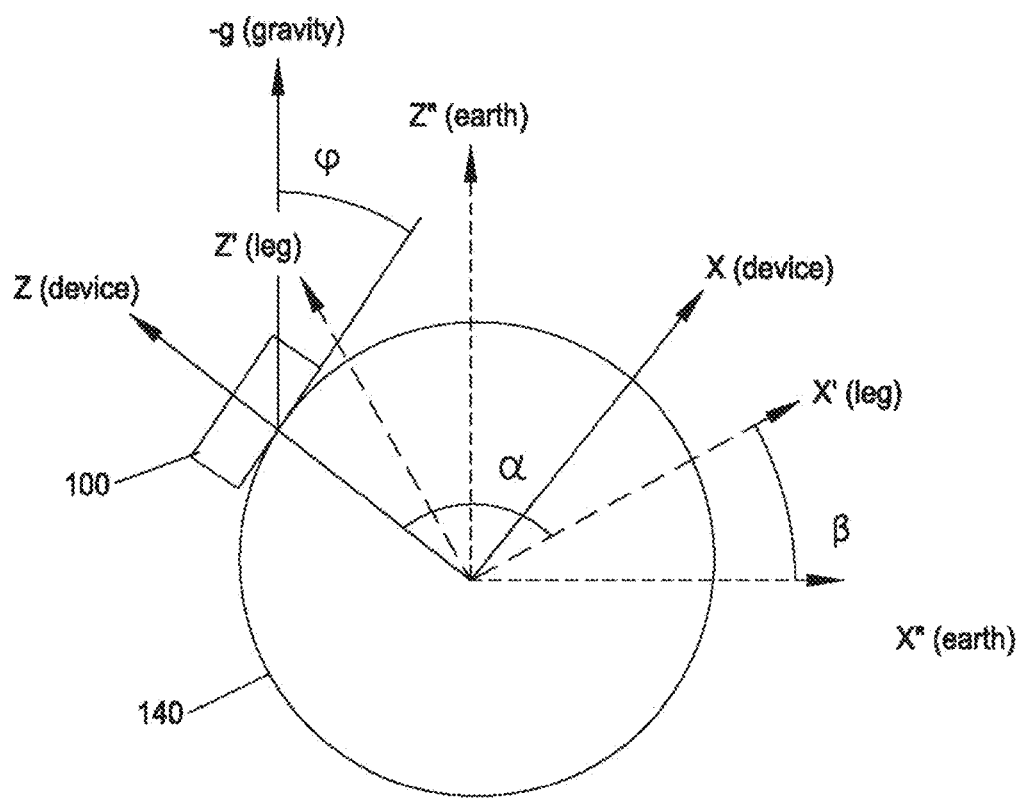
FIG. 9 is a schematic view showing the mathematics for relating the accelerometer rotational angle φ (measured by the accelerometer) to the leg rotational angle β, via a third angle α representing the rotational position of the novel TENS device on the upper calf of a user.

Looking now at FIG. 9, the double-primed coordinate system (i.e., x", y", z", with y" not being seen in FIG. 9 since it extends down the axis of the leg) is fixed to the Earth with gravity along the vertical, the single-primed coordinate system (i.e., x', y', z', with y' not being seen in FIG. 9 since it extends down the axis of the leg) is fixed to the leg, and the unprimed coordinate system (i.e., x, y, z, with y not being seen in FIG. 9 since it extends down the axis of the leg) is fixed to the TENS device measuring $A_{X,T}(t)$ and $\overline{A}_{Z,T}(t)$. The Earth coordinate system has its z"-axis along the vertical, the leg coordinate system has its z'-axis in the direction of the toes, and the leg rotational angle $\beta$ is the angle between the Earth x"-axis and leg x'-axis. The TENS device angle $\alpha$ is the location of the TENS device on the leg measured from the leg x'-axis. Using knowledge of the accelerometer axes in the TENS device, and standard techniques of geometry including the identification of similar triangles, it will be evident to those skilled in the art that these angles are related simply by $\beta=180-\alpha-\varphi$. In each epoch, therefore, these angles are related simply by $\beta_T=180-\alpha-\varphi_T$.

In a preferred embodiment, the following simple procedure is used by processor 515 of user state detector 500 to determine whether the user is on-back through an estimation of the angle $\beta$ when the user is in a "rest-in-bed" state.

Step 1. The user places the TENS device on the lower leg of the user and fastens the strap 110 snugly around their upper calf 140, lies recumbent with the leg nearly horizontal, points their toes vertically upward, and remains still.

Step 2. The user indicates to the TENS device that the aforementioned conditions have been met. This indication may take the form of a series of button presses (e.g., with button 106), a series of taps on compartment 102 detected by the accelerometer 152, or an indication on a smartphone 860 in communication with the TENS device 100.

Step 3: With the toes pointed upright, $\beta \approx 0$, therefore it is trivial to estimate $\hat{\alpha} 180 - \hat{\varphi}$ where $\hat{\varphi}$ is estimated from accelerometer data acquired during the toe-up period. In order to facilitate calculations, put this difference in the range $-180° < \hat{\alpha} \leq 180°$, i.e., if $\hat{\alpha} > 180°$ then subtract 360°, but if $\hat{\alpha} \leq -180°$ then add 360°.

Step 4: In every epoch ending at time T, use this value of $\hat{\alpha}$ to compute $\beta_T = 180 - \hat{\alpha} - \varphi_T$. In order to facilitate comparisons with a threshold, put this difference in the range $-180° < \beta_T \leq 180°$, i.e., if $\beta_T > 180°$ then subtract 360°, but if $\beta_T \leq -180°$ then add 360°.

Step 5: Define a range of values for $\beta_T$ that correspond to the user lying or sleeping on their back. In a preferred embodiment, classify every epoch for which $-80° < \beta_T < 80°$ as "on-back". This range is symmetrical so the algorithm works for placement on either leg. Avoiding ±90° by 10° excludes the values likely to be encountered when a user lies or sleeps on their side. In another preferred embodiment, the thresholds (which would reside at step 930 in FIG. 10) depend upon the leg on which the device is placed. For example, if the device is placed on the left leg, the most likely range of angles while lying on the back is $0° < \beta_T < 80°$. Alternatively, if the device is placed on the right leg, the most likely range of angles while lying on the back is $-80° < \beta_T < 0°$. Using asymmetric thresholds to accommodate the asymmetry of the normal range of motion of the leg relative to the torso may improve the accuracy of the static body rotational position detector.

Step 6: If the user with sleep apnea selects this option for TENS device 100, then when the user is determined to be asleep, i.e., recumbent with low activity, the TENS device notifies the user if they are on their back for more than some set amount of time, e.g., a few minutes. This indication can be in the form of a vibration of the TENS device itself, or an alarm on their smartphone 860, for example.

Step 7: After determining the span(s) of minutes in which the user was likely to be asleep, i.e., recumbent with low activity, determine the fraction of minutes in which the user was determined to be on their back. Report this percentage to this user, e.g., with smartphone 860.

"Out-of-Bed" (OOB) Detector

In one preferred embodiment of the present invention, the 3-axis directions of the accelerometer 152 are known and are fixed in relationship to the lower leg when TENS device 100 is placed on the upper calf 140 of a user: the y-axis is aligned longitudinally along the longitudinal axis of the lower leg of the user; the x-axis is disposed tangential to the surface of the lower leg of the user and perpendicular to the y-axis, and the z-axis points radially away from the surface of the lower leg of the user. Looking now at FIG. 7, where the Earth's gravitational vector g is downward, the elevation angle $\theta$ (172) represents the angle between the positive accelerometer y-axis direction (174) and the true horizontal plane (170). Using the 50 Hz raw data collected from accelerometer 152, which data contains the acceleration due to gravity, processor 515 of user state detector 500 of TENS device 100 can detect when the user is in an upright position, and analyzes the temporal pattern of the acceleration data in order to identify steps (i.e., 610 in FIG. 11) associated with walking (see, for example, Susi M, Renaudin V, and Lachapelle G, Motion mode recognition and step detection algorithms for mobile phone users. Sensors, 2013:13(2): 139-1562). Processor 515 of user state detector 500 of TENS device 100 can also detect sequences of steps taken by a user in order to determine when the user is walking (i.e., 620 in FIG. 11). Individual steps taken by a user may be detected falsely by processor 515 of user state detector 500 of TENS device 100 (e.g., due to other leg movement), however, the "walk detector" function of processor 515 is highly specific, inasmuch as the "walk detector" function of processor 515 requires that the user's detected steps occur regularly and with specific time intervals, in order for processor 515 to determine that the user is walking.

Figure 11:
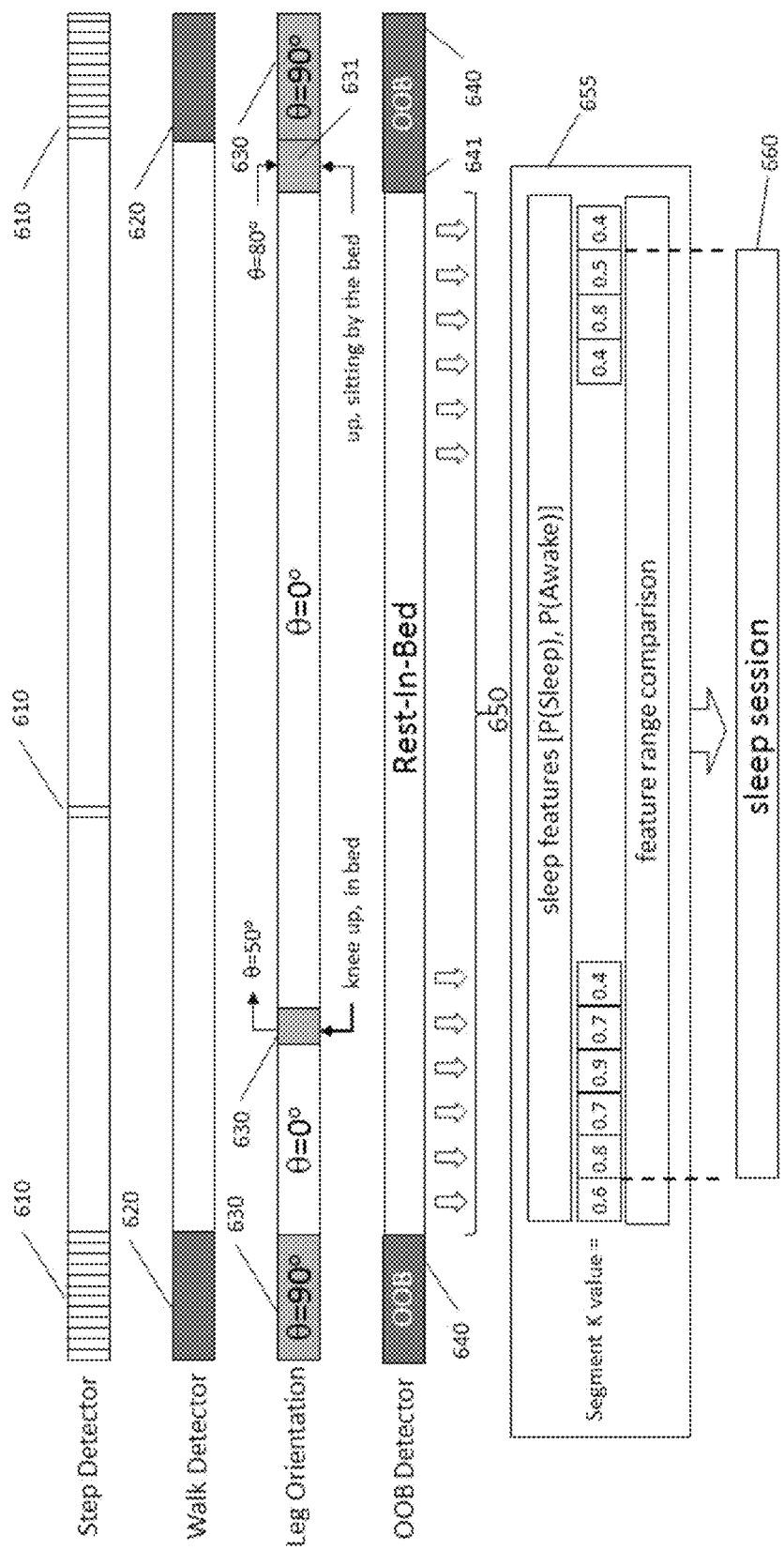
FIG. 11 is a schematic view showing accelerometer data being processed by various components of the sensing unit in order to determine segments of data in an "out-of-bed" (OOB) state and a "rest-in-bed" state.

Using the orientation data stream, each one-minute epoch is classified as "upright" (i.e., 630 and 631 in FIG. 11) if data from accelerometer 152 is processed by processor 515 of user state detector 500 of TENS device 10 and indicates that the absolute value of the mean elevation angle $|\theta| > 45°$. Contiguous sets of the "upright" epochs in which at least one epoch includes walking or at least two epochs include stepping are classified as "out-of-bed" (COB) events 640, 641 (FIG. 11). This use of step and walk detectors makes the detection of "out-of-bed" (COB) events more specific and more accurate. By way of example but not limitation, a user can put their knees up in bed without falsely triggering an "out-of-bed" (COB) event. In addition, epochs for which the mean elevation $\theta > 75°$ (determined by processor 515 using data from accelerometer 152) are classified as "standing" (i.e., the user is standing upright), and are also classified as "out-of-bed" (COB) events 641. Other values for these parameters are possible and are considered to be within the scope of the present invention.

Sleep Detector

Intervals between "out-of-bed" (OOB) events are classified as "rest-in-bed" or "sleep segments" 650. It is understood that a user may not be asleep in each of these "rest-in-bed" or "sleep segments" 650, and the term "sleep segment" implies only that the segments detected by accelerometer 152 will be analyzed (i.e., by processor 515 of user state detector 500 of TENS device 100) in order to determine whether the user is asleep. In the preferred embodiment, each sleep segment 650 is characterized by three basic features: mean activity A, mean elevation θ, and duration D. It should be appreciated that including a lesser number of features (or a greater number of features) is considered to fall within the scope of the present invention. By way of example but not limitation, other possible features include additional measures of activity within a segment (e.g., brief leg movement), measures of changes in leg elevation θ within a segment, and the duration of "out-of-bed" (OOB) events before and/or after a segment.

These features of a given sleep segment 650, which are determined by processor 515 using data from accelerometer 152 and/or gyroscope 163, are passed to a classifier 655 (FIG. 11) which determines whether the given segment meets requirements of sleep (e.g., "goodness-of-fit" of the segment feature parameters to their target ranges). It should be appreciated that the functions of classifier 655 may be implemented by appropriate software programming running on the aforementioned processor 515 of user state detector 500 of TENS device 100, or the functions of classifier 655 may be implemented by another microprocessor of the sort well known in the art with appropriate software programming for providing the functions disclosed herein. In one form of the invention, each segment feature is compared against its own predetermined threshold. In another form of the invention, two or more segment features are evaluated together using a linear or nonlinear classifier function. In one preferred form of the invention, the classifier function is a naïve Bayesian classifier that evaluates all of the features as they occur in a training set, and accounts for the prior probability that the user is asleep given the actual time of day throughout that particular segment; this classifier function then returns the probability that the user is asleep P(Sleep) and the probability that the user is awake P(Wake). Based on these probabilities, each sleep segment 650 is characterized by $K=\log_{10}[P(Sleep)/P(Wake)]$. Each sleep segment 650 is classified by classifier 655 as "Asleep" if and only if $K>K_{th}$. In the simplest embodiment corresponding to the standard naïve Bayes classifier, $K_{th}=0$, in which case $K>0$ is equivalent to the condition P(Sleep)>P(Wake). In one preferred form of the invention, $K_{th}=0.5$ to make the classifier more specific for sleep (i.e., "Asleep"). Other classifiers and values for these parameters are possible, and are considered to fall within the scope of the present invention.

The feature target range(s) and classifier threshold value(s) can be applicable to all users, or tailored to selected group of users, or specific to an individual user, or a combination thereof. For a given user, the feature target range(s) and classifier threshold values may start out (i.e., be preprogrammed) as population default values. These population default values can be updated based on specific indications by the user (e.g., "I am a light sleeper"). Finally, the values can be further refined based on actual user sleep behavior previously measured by TENS device 100 (e.g., a particular user's likely time of day for sleep calculation is modified by the user's prior history of sleep onset time).

A sleep session 660 is a contiguous time interval during which the user is in bed for sleeping. In theory, a given sleep session 660 corresponds to the standard clinical definition of "time in bed". In practice, a given sleep session 660 it is detected as a series of sleep segments for which the starting and ending segments have $K>K_{th}$. This definition allows a given sleep session 660 to include some "out-of-bed" (OOB) events as may normally occur during the night, and two "out-of-bed" (OOB) events may be separated by a brief sleep segment, with $K<K_{th}$. In addition, because users may watch television or read with their leg(s) elevated, and users may be resting before bed (but not asleep), some sleep segments at the beginning of the night may have $K>K_{th}$, however, the corresponding K values will typically be lower than those of sleep segments later in the night which are more clearly sleep. In one preferred form of the invention, there are logical conditions which need to be met in order to start a sleep session 660 which excludes those sleep segments corresponding to reading or watching television in bed; this can be accomplished by examining the history and trend of the K values recorded and analyzed by TENS device 100. By way of example but not limitation, a given sleep session 660 starts with the first sleep segment having a more stringent requirement of $K>0.75$, and ends when an "out-of-bed" (OOB) event is detected which lasts more than 15 minutes, with the additional condition that the last sleep segment included must have $K>K_{th}$. Other logical schemes and values for these parameters for the first sleep segment, the last sleep segment and intermediate sleep segments are possible and fall within the scope of the present invention.

Some users may have one (or more) long "out-of-bed" (OOB) event(s) during a given sleep session 660 (i.e., during the night while the user is sleeping) which results in TENS device 100 registering two or more sleep sessions 660. In one preferred form of the invention, there are logical conditions which may be applied in order to merge the data for multiple sleep sessions 660. By way of example but not limitation, two sleep sessions 660 lasting at least 3 hours each and separated by an "out-of-bed" (OOB) event lasting less than 1 hour may be merged together to form one sleep session 660 in which the intervening "out-of-bed" (OOB) event is classified as "awake". After the total (i.e., the merged) sleep session 660 is defined, sleep metrics are computed by TENS device 100 (e.g., by aforementioned processor 515 of user state detector 500 of TENS device 100) and reported to the user.

Real-Time Estimation of Sleep Probability

In order to control the stimulation delivered by TENS device 100 to a user in real-time during a sleep session 660, the TENS device 100 uses the information available for each minute (i.e., each epoch) to estimate the probability that the user is sleeping, P(Sleep). In one embodiment, sleep probability (i.e., P(Sleep)) as a function of time depends on the same three features used to assign a K value to a sleep segment as described above (i.e., mean activity A, mean elevation θ, and duration D). Because P(Sleep) depends in part upon the duration of a particular sleep segment, P(Sleep) increases gradually following an "out-of-bed" (OOB) event. P(Sleep) increases with time more quickly if TENS device 100 measures a lower mean activity level A and a mean elevation θ value closer to zero.

Figure 12:
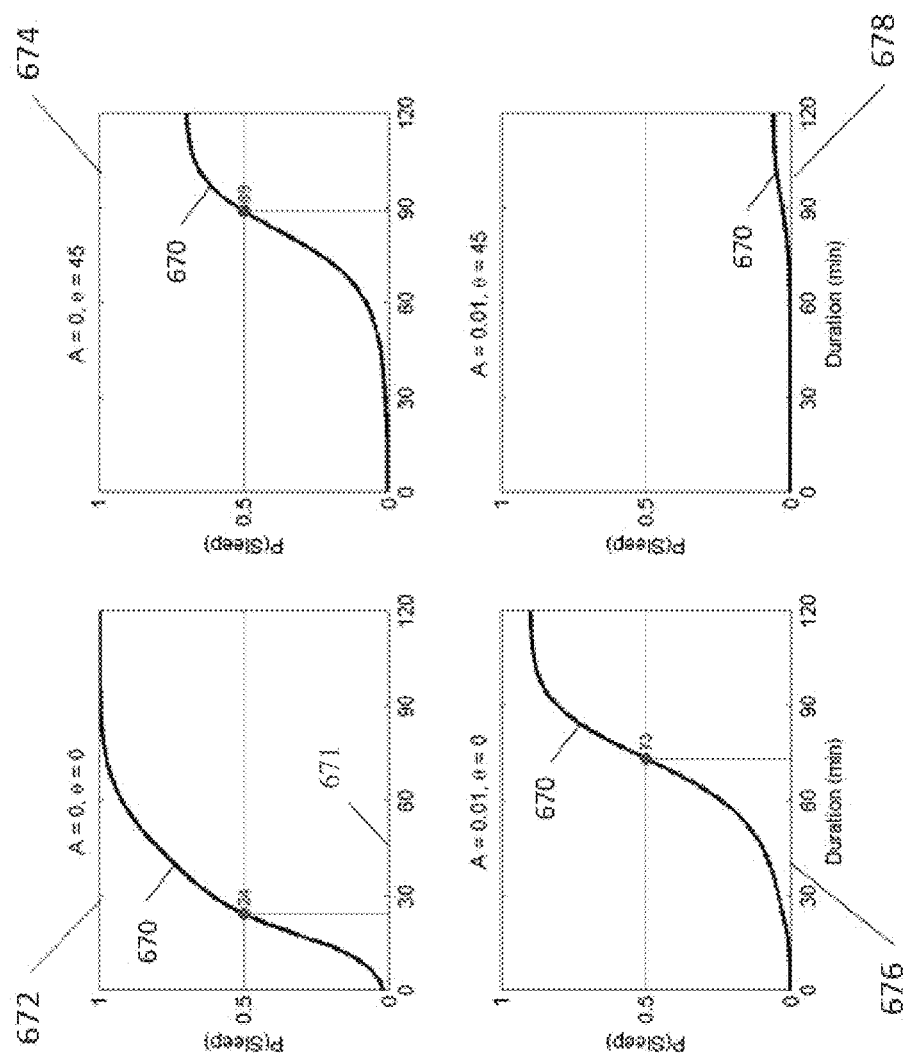
FIG. 12 is a schematic view showing that the sleep probability of accelerometer data epochs increases with time within the "rest-in-bed" state, with each subplot of sleep probability being characterized by the mean leg activity feature A and mean leg elevation angle feature θ as determined by processing the accelerometer data.

FIG. 12 shows P(Sleep) 670 for a given user as a function of time duration 671 since the last recorded "out-of-bed"

(OOB) event, in four model cases: (i) mean activity A=0 and mean elevation θ=0°, (ii) mean activity A=0 and mean elevation θ=45°, (iii) mean activity A=0.01 g and mean elevation θ=0°, and (iv) mean activity A=0.01 g and mean elevation θ=45°. The case 672 (A=0 and θ=0°) corresponds to ideal restful sleep. The extreme case 678 (A=0.01 g and θ=45°) corresponds to a user lying in bed with their knees up and very restless sleep. In the ideal case 672, P(Sleep) =0.5 at 24 minutes following the "out-of-bed" (OOB) event. In the extreme case, P(Sleep)<0.5 indefinitely. In the mixed cases 674 and 676, P(Sleep)=0.5 at 73-89 minutes following an "out-of-bed" (OOB) event.

Real-Time Control of Stimulation Level

In one preferred form of the invention, a flag (i.e., a variable) called "AsleepForStim" is defined to indicate the real-time sleep state of the user in order to control the stimulation intensity (e.g., a flag "AsleepForStim" is set by the software running on processor 515 of TENS device 100). Following an "out-of-bed" (OOB) event, for each minute (i.e., epoch), the TENS device 100 computes P(Sleep). When P(Sleep)>0.5, the AsleepForStim flag is set "true". The AsleepForStim flag remains "true" until an "out-of-bed" (OOB) event is detected and has lasted for at least 15 minutes, then the AsleepForStim flag is set "false". Consequently, the AsleepForStim flag will generally be "true" throughout a given sleep session 660, including any brief "out-of-bed" (OOB) events during a given night (i.e., a given sleep session).

When stimulation is scheduled to start, TENS device 100 checks the value of the AsleepForStim flag (i.e., to determine whether the flag is set to "true" or "false"). If the AsleepForStim flag is "false", then the stimulation level will be unchanged. If AsleepForStim flag is "true", the stimulation level will be reduced (unless the user chooses to disable this adaptive stimulation feature of TENS device 100).

Furthermore, if the AsleepForStim flag is "true" and the user enables the adaptive therapy onset mode (i.e., enables TENS device 100 to deliver adaptive stimulation depending upon user wake/sleep state), scheduled onset time for next therapy may be postponed based on a real-time measure of sleep quality called "sleep fragmentation", as will hereinafter be discussed in further detail.

Real-Time Calculation of Sleep Fragmentation

Sleep fragmentation refers to brief arousals or awakenings that disrupt the normal sleep architecture, and often occurs often in people experiencing chronic pain. The present invention provides the user with the option to start therapy during sleep only when sleep is fragmented. This option balances the goals of using TENS device 100 to reduce pain and improve sleep, while minimizing the possibility that the sensation of stimulation may itself disturb sleep.

In one preferred form of the invention, when stimulation is scheduled to start, the TENS device 100 checks the value of the flag for AsleepForStim. If the flag for AsleepForStim is "true" and if TENS device 100 has been on the user's skin for at least an hour (i.e., electrode array 120 of TENS device 100 has been in contact with the user's skin for at least an hour), processor 515 of TENS device 100 determines a value for a flag called "SleepFragmented" in the prior hour. If the SleepFragmented flag is determined to be "false", i.e., if sleep is very restful, then onset of stimulation is postponed. TENS device 100 then checks the flag for SleepFragmented status every 5 minutes. When either the flag for AsleepForStim is "false" (i.e., the user is awake), or the flag for SleepFragmented is "true" (i.e., sleep is no longer restful), stimulation by TENS device 100 is permitted to start. In this way, stimulation is delivered by TENS device 100 only as needed.

During a given sleep session 660, a user is considered to be awake if the user is either "out-of-bed" (OOB), or if the user's mean activity in a one-minute epoch A>0.01. A more sensitive measure of brief arousals available from accelerometer data is leg movements (LM), computed using the 10 Hz activity stream, in which the effect of gravity has been removed. A leg movement (LM) is defined as an event in which the activity detected by TENS device 100 exceeds a predetermined threshold A2 and then falls below a predetermined threshold A1. In one preferred form of the invention, the predetermined thresholds are A1=0.02, A2=0.03, and there are no limits on its duration. In practice, active epochs usually contain numerous events that meet this definition of leg movement (LM), so epochs with one or more leg movement (LM) events normally include awake epochs as well as epochs with brief arousals. In a preferred embodiment, the aforementioned Boolean flag called SleepFragmented is "true" if and only if, in the last hour, the fraction of epochs with one or more leg movement (LM) is greater than 40%. Other definitions of sleep fragmentation and values of these parameters are possible and considered to fall within the scope of the present invention. In addition, these values may be set by TENS device 100, or these values may be modified by the user.

Figure 13:
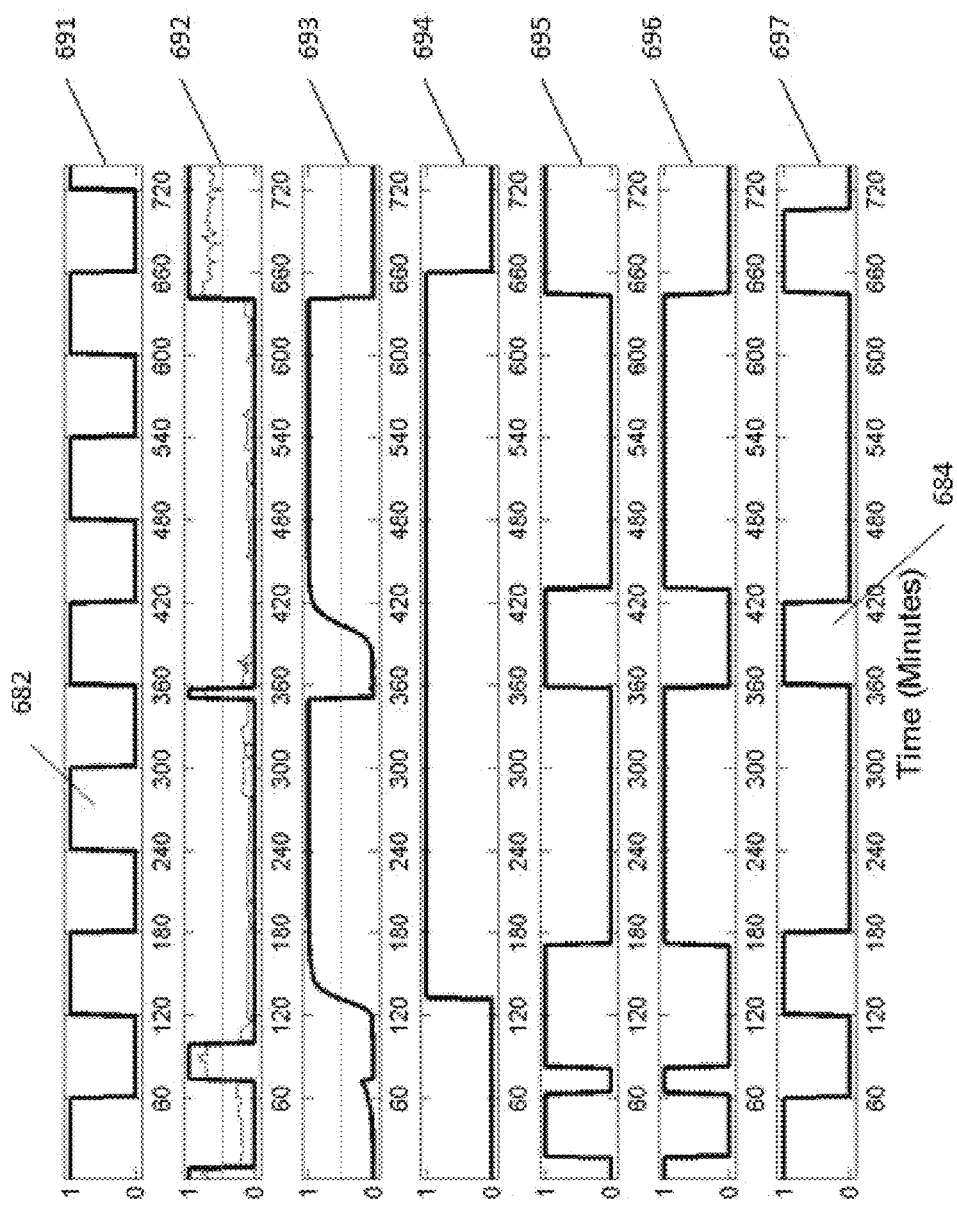
FIG. 13 is a schematic view showing exemplary operation of the novel TENS device, including its user state (i.e., "out-of-bed" state and "rest-in-bed" state), fragmented sleep quality (poor sleep quality) indicator, and modification of the TENS therapy session start time.

FIG. 13 provides an illustrative example of the adaptive behavior of the therapy onset based on user sleep state. Default therapy sessions are shown in trace 691. User "out-of-bed" (OOB) events are marked in trace 692 (i.e., when the trace value is equal to 1). Sleep probability based on user activity level, leg elevation, and "out-of-bed" (OOB) events is shown as trace 693. The AsleepForStim flag is shown as trace 694 (i.e., the AsleepForStim flag is "true" when the trace value equals 1 and "false" when trace value equals 0). The SleepFragmented flag is shown as trace 695 (i.e., the SleepFragmented flag is "true" when the trace value equals 1 and "false" when trace value equals 0). The OnsetDelay flag (which is the logic inverse of the SleepFragmented flag) is shown as trace 696 (i.e., the OnsetDelay flag is "true" when the trace value equals 1 and "false" when trace value equals 0). Finally, adaptive therapy sessions are shown as trace 697.

The sleep probability trace 693 is also shown in FIG. 13, with P(Sleep)>0.5 corresponding to "true" (i.e., "1") for the first time at a point near 132 minutes. The AsleepForStim flag trace 694 turns true (i.e., "1") at 132 minutes, and remains true, even during the brief "out-of-bed" (OOB) event from 351-357 minutes (shown in trace 692). An extended "out-of-bed" (OOB) event starts at 642 minutes, and the AsleepForStim flag becomes "false" at 662 minutes (shown in trace 694).

The onset of the scheduled therapy session 682 which would have occurred at the $240^{th}$ minute is delayed to the $360^{th}$ minute. Specifically, for each minute (i.e., epoch) when a therapy session was scheduled to start (i.e., at the time instance when the value of trace 691 transitions from 0 to 1), if the OnsetDelay flag (trace 696) is still "true", the start of the therapy session is delayed. Since the OnsetDelay flag 696 becomes true at 171 minutes, and becomes false at 359 minutes, the scheduled therapy session (trace 691) at the $240^{th}$ minute is delayed, and an actual therapy session 684 begins at the $360^{th}$ minute.

Modifications of the Preferred Embodiments

It will be appreciated that the present invention provides a transcutaneous electrical nerve stimulator with automatic assessment of sleep patterns and sleep characteristics based on monitoring of leg activities and leg orientations. Leg orientations include leg elevation and leg rotation state, and changes in leg elevation and leg rotation states. The TENS stimulator may be pre-programmed to modify its operations in response to the detected user leg activities and leg positions during bed time. Individual aspects of the TENS stimulator operations (e.g., stimulation onset, stimulation pulse intensity, and stimulation session duration) are modified based on specific sleep characteristics. However, these operating parameters can be modified simultaneously. In addition, leg orientation and leg activities are used to assess sleep quality and sleep position, all are important aspects to improve sleep and health. Leg activity patterns can also be used to diagnose sleep disorders such as periodic leg movement and the TENS stimulator can be used to alleviate excessive leg movement activities that are disruptive to sleep.

While most sleep applications have a goal of prolonging good quality sleep, it may also be desirable to regulate the duration of good quality sleep each night. Another realization of the present invention is to provide the user with feedback when the total duration of good sleep (i.e., non-fragmented sleep) reaches a target range. The feedback provided to the user can be in the form of mechanical vibrations from a vibration motor (i.e., haptic feedback). The feedback can also be in the form of electrical stimulation (i.e., a stimulation pulse delivered by TENS device 100). In yet another realization of the present invention, feedback to the user is provided when a minimum time period of good sleep is achieved and the sleep quality is transitioning from non-fragmented sleep to fragmented sleep.

The present invention can also be realized without the nerve stimulation functionality. Body movement and position can be monitored and quantified using the present invention without the need of nerve stimulation. The monitoring apparatus (device) can also be placed in other body positions like upper arm of either limb.

Furthermore, many additional changes in the details, materials, steps and arrangements of parts, which have been herein described and illustrated in order to explain the nature of the present invention, may be made by those skilled in the art while still remaining within the principles and scopes of the invention.

What is claimed is:

1. Apparatus for providing transcutaneous electrical nerve stimulation (TENS) therapy to a user, said apparatus comprising:
    a housing;
    an application unit for providing mechanical coupling between said housing and the user's body;
    a stimulation unit for electrically stimulating at least one nerve of the user;
    a sensing unit for (i) sensing the body movement and body orientation of the user to determine whether the user is in an "out-of-bed" state or a "rest-in-bed" state, and (ii) analyzing sleep characteristics of the user during said "rest-in-bed" state; and
    a feedback unit for at least one of (i) providing the user with feedback in response to said analysis of said sleep characteristics of the user, and (ii) modifying the electrical stimulation provided to the user by said stimulation unit in response to said analysis of said sleep characteristics of the user;
    wherein said sleep characteristics comprise a likelihood measure of the sleep quality of the user.

2. Apparatus according to claim 1 wherein said application unit is a flexible band.

3. Apparatus according to claim 1 wherein said application unit determines whether said housing is mechanically coupled to the body of the user.

4. Apparatus according to claim 3 wherein a mechanical element determines whether said housing is mechanically coupled to the user's body.

5. Apparatus according to claim 4 wherein said mechanical element is a tension gauge.

6. Apparatus according to claim 3 wherein an electrical element determines whether said housing is mechanically coupled to the body of the user.

7. Apparatus according to claim 1 wherein the user is determined to be in said "out-of-bed" state when a body orientation angle exceeds a threshold.

8. Apparatus according to claim 1 wherein the user is determined to be in said "out-of-bed" state when a body movement pattern matches a pattern for walking.

9. Apparatus according to claim 1 wherein the user is determined to be in said "out-of-bed" state when a body orientation angle exceeds a threshold and when body movement pattern matches a pattern for stepping.

10. Apparatus according to claim 1 wherein said sensing unit uses data from an electromechanical sensor.

11. Apparatus according to claim 10 wherein the determination of whether said housing is mechanically coupled to the body of the user determines the usability of the data from said electromechanical sensor.

12. Apparatus according to claim 10 wherein said electromechanical sensor is an accelerometer.

13. Apparatus according to claim 10 wherein said electromechanical sensor is a gyroscope.

14. Apparatus according to claim 10 wherein said electromechanical sensor comprises both an accelerometer and a gyroscope.

15. Apparatus according to claim 10 wherein said sensing unit determines the body orientation angle of the user with an analysis unit operating on earth gravitational acceleration measurements from said electromechanical sensor.

16. Apparatus according to claim 10 wherein said sensing unit determines a movement pattern of the user with an analysis unit operating on said data from said electromechanical sensor.

17. Apparatus according to claim 16 wherein said movement pattern is determined to be a walking pattern when a processed feature of said data is determined to be stepping continuously for a period of time.

18. Apparatus according to claim 17 wherein said processed feature is determined to be a stepping pattern when filtered components of the data from said electromechanical sensor match a target temporal pattern.

19. Apparatus according to claim 1 wherein said sleep characteristics for a time segment are determined based on at least one feature selected from the group consisting of (i) mean leg activity, (ii) mean leg elevation, (iii) leg rotation amount, and (iii) duration of the time segment.

20. Apparatus according to claim 19 wherein analyzing said sleep characteristics comprises utilizing a Bayesian classifier to compare at least one feature to a predetermined classifier threshold.

21. Apparatus according to claim 20 wherein said predetermined classifier threshold is a function of the time elapsed from the onset of said "rest-in-bed" state.

22. Apparatus according to claim 20 wherein said predetermined classifier threshold is a function of the health profile of the user.

23. Apparatus according to claim 20 wherein said predetermined classifier threshold is a function of past sleep characteristics of the user.

24. Apparatus according to claim 20 wherein said sleep characteristics of said time segment is determined to be "good" when the output of said Bayesian classifier exceeds said predetermined classifier threshold for said time segment.

25. Apparatus according to claim 1 wherein said analysis of sleep characteristics determines sleep quality for a time segment.

26. Apparatus according to claim 24 wherein said sleep quality is determined to be fragmented when the percentage of "good" sleep over said time segment is below a predetermined threshold.

27. Apparatus according to 25 wherein said time segment is at least one hour.

28. Apparatus according to claim 24 wherein said feedback unit calculates the accumulated time during which sleep quality of the user is classified as "good".

29. Apparatus according to claim 28 wherein said feedback unit is activated when the said accumulated time exceeds a predetermined threshold.

30. Apparatus according to claim 1 wherein said feedback unit provides feedback to the user via an alert delivered to the user through at least one selected from the group consisting of a smartphone and another connected device.

31. Apparatus according to claim 1 wherein said feedback unit provides feedback to the user in the form of mechanical vibrations provided to the user.

32. Apparatus according to claim 1 wherein said feedback unit provides feedback to the user in the form of electrical stimulation provided to the user.

33. Apparatus according to claim 26 wherein said feedback unit modifies said electrical stimulation provided to the user when said sleep quality is not fragmented.

34. Apparatus according to claim 33 wherein said electrical stimulation is modified to change stimulation intensity.

35. Apparatus according to claim 33 wherein said electrical stimulation is modified to change stimulation frequency.

36. Apparatus according to claim 33 wherein said electrical stimulation is modified to change the stimulation onset time.

37. Apparatus according to claim 36 wherein said stimulation onset time change is to postpone a scheduled stimulation start time.

38. A method for applying transcutaneous electrical nerve stimulation to a user, said method comprising the steps of:
applying a stimulation unit and a sensing unit to the body of the user;
using said stimulation unit to deliver electrical stimulation to the user so as to stimulate one or more nerves of the user;
analyzing electromechanical sensing data collected by said sensing unit in order to (i) determine the body orientation of the user, and (ii) quantify body activity levels so as to determine whether the user is in an "out-of-bed" state, wherein the user is awake, or a "rest-in-bed" state, wherein the user is at rest or asleep, whereby to determine the quality and duration of sleep of the user during the "rest-in-bed" state; and
modifying the electrical stimulation delivered by said stimulation unit based on said sleep quality and said duration of the sleep of the user during the "rest-in-bed" state.

39. Apparatus for monitoring the sleep patterns of a user, said apparatus comprising:
a housing;
an application unit for providing mechanical coupling between said housing and the user's body;
a sensing unit carried by the housing for (i) sensing the body movement and body orientation of the user to determine whether the user is in an "out-of-bed" state or a "rest-in-bed" state, and (ii) analyzing sleep characteristics of the user during said "rest-in-bed" state; and
a feedback unit for providing the user with feedback in response to said analysis of said sleep characteristics of the user.

40. A method for monitoring the sleep patterns of a user, said method comprising of the steps of:
applying a sensing unit and a feedback unit to the body of a user;
using said sensing unit to determine the body movement and body orientation of the user to (i) determine whether the user is in an "out-of-bed" state or a "rest-in-bed" state, and (ii) analyze sleep characteristics of the user during said "rest-in-bed" state; and
providing the user with feedback via said feedback unit in response to said analysis of said sleep characteristics of the user.

41. Apparatus for providing transcutaneous electrical nerve stimulation (TENS) therapy to a user, said apparatus comprising:
a housing;
an application unit for providing mechanical coupling between said housing and the leg of a user;
a stimulation unit for electrically stimulating at least one nerve of the user; and
a sensing unit for (i) sensing the leg orientation and leg motion of the user to determine whether the user is in an "out-of-bed" state or a "rest-in-bed state", wherein sensing the leg orientation of the user comprises determining the leg elevation and leg rotation of the user, and further wherein sensing the leg motion of the user comprises determining the net activity and leg movements of the user, and (ii) analyzing sleep characteristics of the user during said "rest-in-bed" state; and
a controller for modulating said stimulation unit based on said determinations of sleep characteristics made by said sensing unit.

42. Apparatus for providing transcutaneous electrical nerve stimulation (TENS) therapy to a user, said apparatus comprising:
a housing;
an application unit for providing mechanical coupling between said housing and the user's body;
a stimulation unit for electrically stimulating at least one nerve of the user;
a sensing unit for (i) sensing the body movement and body orientation of the user to determine whether the user is in an "out-of-bed" state or a "rest-in-bed" state, and (ii) analyzing sleep characteristics of the user during said "rest-in-bed" state; and
a feedback unit for at least one of (i) providing the user with feedback in response to said analysis of said sleep characteristics of the user, and (ii) modifying the electrical stimulation provided to the user by said stimulation unit in response to said analysis of said sleep characteristics of the user;

wherein said sleep characteristics comprise a likelihood measure of the sleep quality of the user;

wherein said sleep characteristics for a time segment are determined based on at least one feature selected from the group consisting of (i) mean leg activity, (ii) mean leg elevation, (iii) leg rotation amount, and (iii) duration of the time segment;

wherein analyzing said sleep characteristics comprises utilizing a Bayesian classifier to compare at least one feature to a predetermined classifier threshold;

wherein said predetermined classifier threshold is a function of at least one from the group consisting of the time elapsed from the onset of said "rest-in-bed" state, the health profile of the user, and past sleep characteristics of the user.

43. Apparatus for providing transcutaneous electrical nerve stimulation (TENS) therapy to a user, said apparatus comprising:
a housing;
an application unit for providing mechanical coupling between said housing and the user's body;
a stimulation unit for electrically stimulating at least one nerve of the user;
a sensing unit for (i) sensing the body movement and body orientation of the user to determine whether the user is in an "out-of-bed" state or a "rest-in-bed" state, and (ii) analyzing sleep characteristics of the user during said "rest-in-bed" state; and
a feedback unit for at least one of (i) providing the user with feedback in response to said analysis of said sleep characteristics of the user, and (ii) modifying the electrical stimulation provided to the user by said stimulation unit in response to said analysis of said sleep characteristics of the user;

wherein said sleep characteristics comprise a likelihood measure of the sleep quality of the user;

wherein said sleep characteristics for a time segment are determined based on at least one feature selected from the group consisting of (i) mean leg activity, (ii) mean leg elevation, (iii) leg rotation amount, and (iii) duration of the time segment;

wherein analyzing said sleep characteristics comprises utilizing a Bayesian classifier to compare at least one feature to a predetermined classifier threshold;

wherein said sleep characteristics of said time segment is determined to be "good" when the output of said Bayesian classifier exceeds said predetermined classifier threshold for said time segment.

44. Apparatus according to claim 43 wherein said sleep quality is determined to be fragmented when the percentage of "good" sleep over said time segment is below a predetermined threshold.

45. Apparatus according to claim 43 wherein said feedback unit calculates the accumulated time during which sleep quality of the user is classified as "good".

46. Apparatus according to claim 45 wherein said feedback unit is activated when the said accumulated time exceeds a predetermined threshold.

47. Apparatus according to claim 44 wherein said feedback unit modifies said electrical stimulation provided to the user when said sleep quality is not fragmented.

48. Apparatus according to claim 47 wherein said electrical stimulation is modified to change at least one from the group consisting of stimulation intensity, stimulation frequency and stimulation onset time.

49. Apparatus according to claim 48 wherein said stimulation onset time change is to postpone a scheduled stimulation start time.

* * * * *